US012644045B2

(12) United States Patent
Tang et al.

(10) Patent No.: US 12,644,045 B2
(45) Date of Patent: Jun. 2, 2026

(54) FLUORESCENT COMPOUNDS AND APPLICATION THEREOF

(71) Applicant: The Hong Kong University of Science and Technology, Hong Kong (CN)

(72) Inventors: Benzhong Tang, Hong Kong (CN); Zheng Zhao, Hong Kong (CN); Hao Xing, Hong Kong (CN); Ying Yu, Hong Kong (CN)

(73) Assignee: THE HONG KONG UNIVERSITY OF SCIENCE AND TECHNOLOGY, Hong Kong (CN)

( * ) Notice: Subject to any disclaimer, the term of this patent is extended or adjusted under 35 U.S.C. 154(b) by 982 days.

(21) Appl. No.: 17/476,854

(22) Filed: Sep. 16, 2021

(65) Prior Publication Data

US 2022/0145173 A1 May 12, 2022

Related U.S. Application Data

(60) Provisional application No. 63/204,992, filed on Nov. 6, 2020.

(51) Int. Cl.

| | |
|---|---|
| ***C09K 11/06*** | (2006.01) |
| ***G01N 21/64*** | (2006.01) |
| ***G01N 33/52*** | (2006.01) |
| ***H10K 50/11*** | (2023.01) |

(52) U.S. Cl.

CPC .......... *C09K 11/06* (2013.01); *G01N 21/6458* (2013.01); *G01N 21/6486* (2013.01); *G01N 33/52* (2013.01); *H10K 50/11* (2023.02); *C09K 2211/1051* (2013.01)

(58) Field of Classification Search

CPC ............ C09K 11/06; C09K 2011/1051; H10K 50/11; G01N 21/6458; G01N 21/6486; G01N 33/52

See application file for complete search history.

(56) References Cited

U.S. PATENT DOCUMENTS

| | | | | |
|---|---|---|---|---|
| 7,223,484 | B2 * | 5/2007 | Stossel | C07D 513/04 548/134 |
| 9,722,184 | B2 * | 8/2017 | Fujita | C07D 513/22 |
| 2018/0335654 | A1 * | 11/2018 | Kirsch | F24S 50/80 |
| 2019/0127586 | A1 * | 5/2019 | Kirsch | C09B 57/00 |
| 2019/0189925 | A1 * | 6/2019 | Wang | H10K 85/657 |

FOREIGN PATENT DOCUMENTS

| | | | | |
|---|---|---|---|---|
| JP | 2005038658 A | * | 2/2005 | H05B 33/14 |
| WO | WO-2016091345 A1 | * | 6/2016 | C07D 513/04 |
| WO | WO-2017174619 A1 | * | 10/2017 | C09B 57/00 |
| WO | WO-2018041768 A1 | * | 3/2018 | C07D 241/42 |

OTHER PUBLICATIONS

Machine translation JP 2005038658 A published Feb. 10, 2005 (Year: 2005).*

* cited by examiner

*Primary Examiner* — Jane L Stanley
(74) *Attorney, Agent, or Firm* — WPAT, PC

(57) ABSTRACT

The present invention discloses donor-acceptor structured, aggregated-induced emission fluorescent compounds with deep-red (DR) or near-infrared (NIR). The present invention also shows application in bio-imaging or optoelectronic devices with the fluorescent compounds.

13 Claims, 21 Drawing Sheets

Two-photon

One-photon

FLUORESCENT COMPOUNDS AND APPLICATION THEREOF

CROSS REFERENCE TO RELATED APPLICATIONS

This application claims priority to and the benefit of U.S. Provisional Patent Application Ser. No. 63/204,992 filed on Nov. 6, 2020, the disclosure of which is incorporated by reference in its entirety.

TECHNICAL FIELD

The present invention relates to donor-acceptor structured, aggregated-induced emission fluorescent compounds with deep-red (DR) or near-infrared (NIR) emission and applies them into bio-imaging or optoelectronic devices.

BACKGROUND

Deep red and near-infrared red emitters are of great importance in many areas. For bio-imaging, they have the advantages of deeper penetration depth and smaller photodamage to the tissues. For optoelectronic devices, highly efficient red and NIR luminogens are in great demand compared with other colors.

Due to the energy gap law, the longer the emission wavelength, the lower the quantum yield and therefore the lower device efficiency. Charge transfer by donor-acceptor structure is a commonly used and effective way to construct the red and NIR emitters. Compared with merely extending the π conjugation to expand the emission wavelength, D-A moieties can realize red emission with smaller molecules and easier modification.

Usually, for donors, the choices are diverse with different combinations. On the other hand, suitable acceptors with strong electron-withdrawing ability and easy accessibility are limited. Great efforts have been made to develop new types of acceptors to expand the library of red/NIR luminogens.

SUMMARY

In order to provide new, easy synthesizable, for constructing deep-red/near-infrared luminogens, the present invention provides various embodiments described below.

In one embodiment, a fluorescent compound is provided. The fluorescent compound exhibits aggregation induced emission properties, the fluorescent compound having formula (I) or formula (II):

(I)

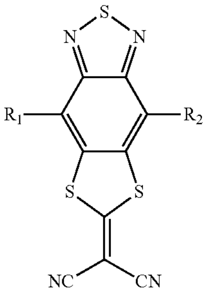

-continued (II)

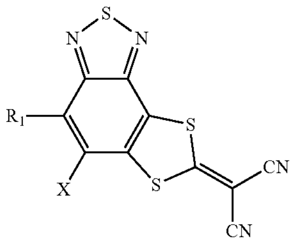

wherein $R_1$ is selected from the group consisting of:

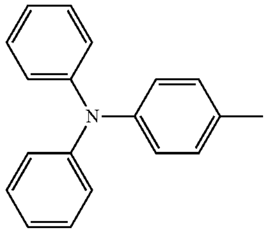

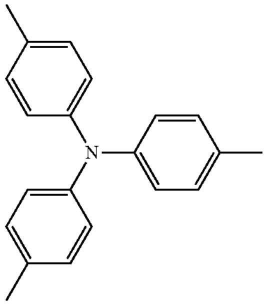

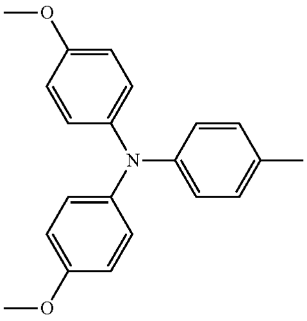

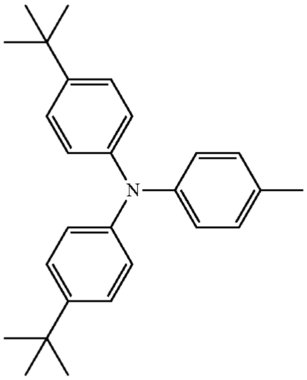

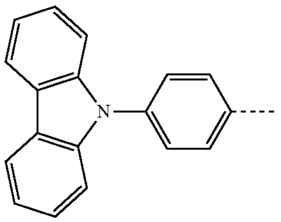

-continued

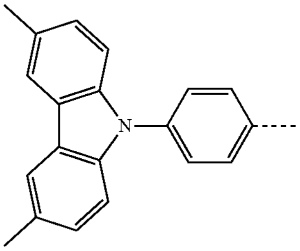

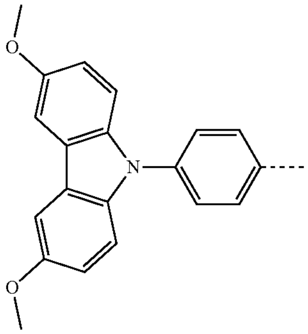

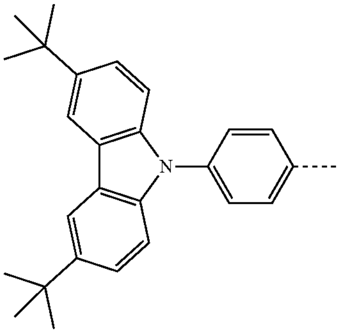

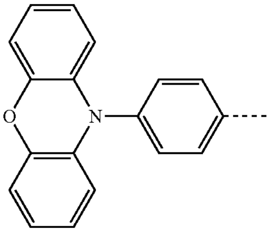
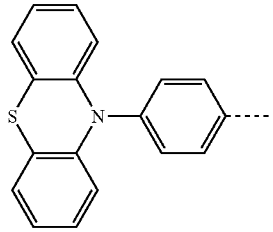

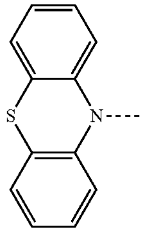
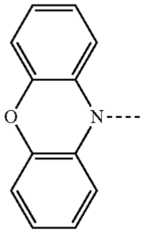

wherein $R_2$ is selected from the group consisting of:

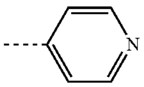
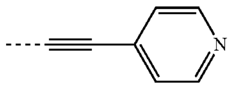

-continued

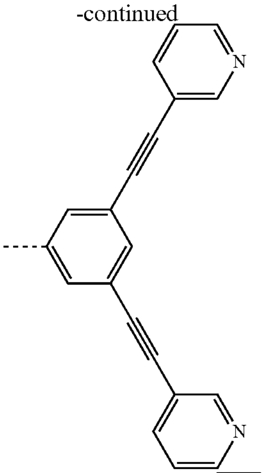

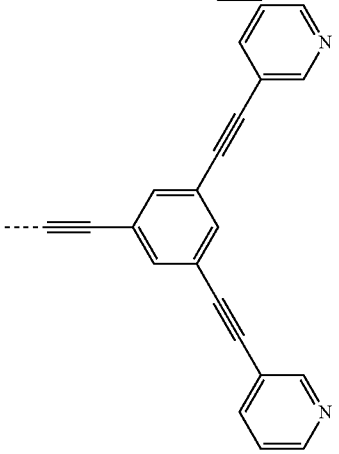

wherein X is selected from the group consisting of —H, —F, and —Cl.

In another embodiment, a method of cellular imaging is provided. The method comprising:

contacting a target cell with the above-mentioned fluorescent compound; and identifying a target of interest in the target cell using an imaging method.

In still another embodiment, an organic electroluminescent device is provided. The method organic electroluminescent device comprising a light-emitting layer comprising:

at least one host material; and at least one thermally activated delayed fluorescence (TADF) material comprising the above-mentioned fluorescent compound.

The above description is only an outline of the technical schemes of the present invention. Preferred embodiments of the present invention are provided below in conjunction with the attached drawings to enable one with ordinary skill in the art to better understand said and other objectives, features and advantages of the present invention and to make the present invention accordingly.

BRIEF DESCRIPTION OF THE DRAWINGS

The present invention can be more fully understood by reading the following detailed description of the preferred embodiments, with reference made to the accompanying drawings, wherein.

Ex vivo fatty liver tissue imaging.

OLED data of TBSMCN in different device structures.

Figure 27A:
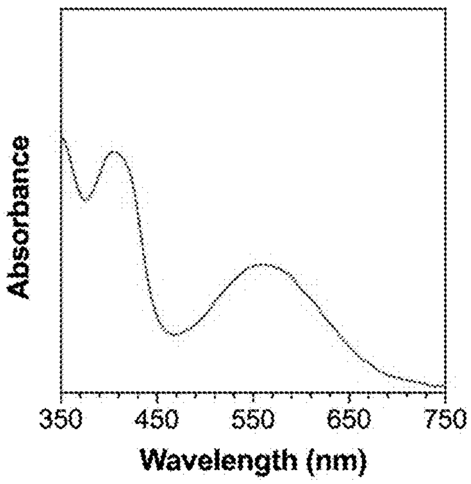
Figure 27B:
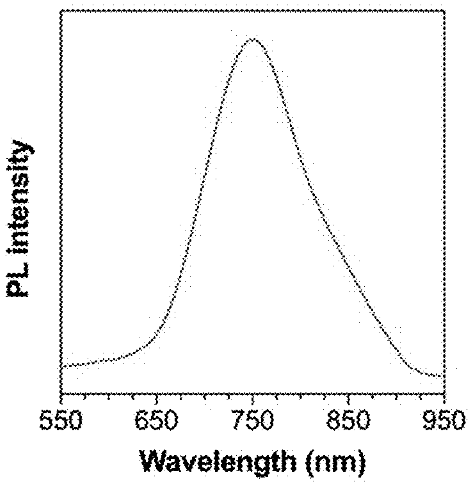

UV spectrum FIG. 27A and PL spectrum FIG. 27B of TBSMPy in film state. $\lambda_{ex}$=560 nm.

Figure 28A:
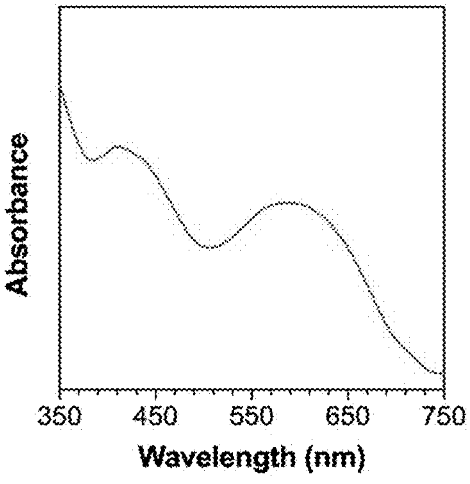
Figure 28B:
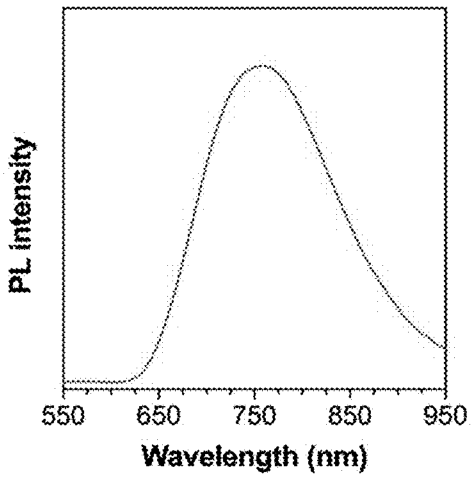

UV spectrum FIG. 28A and PL spectrum FIG. 28B of TBSMDPy in film state. $\lambda_{ex}$=580 nm.

DETAILED DESCRIPTION

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

It should be understood that the order of steps or order for performing certain actions is immaterial so long as the present teachings remain operable. Moreover, two or more steps or actions may be conducted simultaneously.

In a first embodiment of the present invention, a fluorescent compound is provided. The fluorescent compound exhibits aggregation induced emission properties, the fluorescent compound having formula (I) or formula (II):

(I)

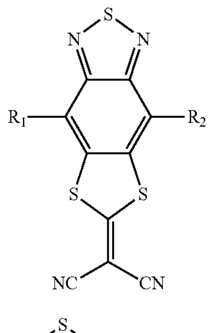

(II)

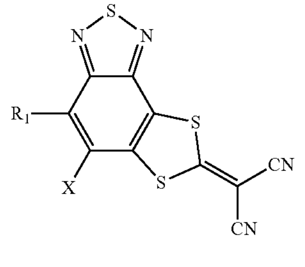

wherein $R_1$ is selected from the group consisting of:
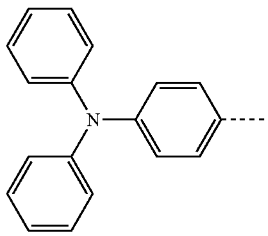
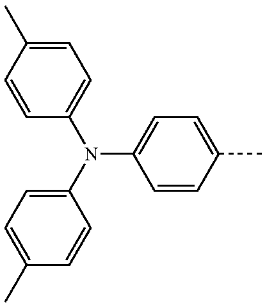
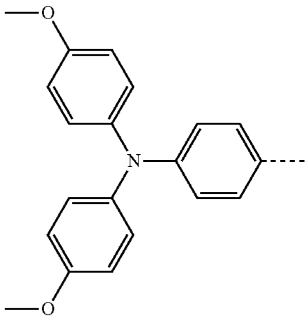
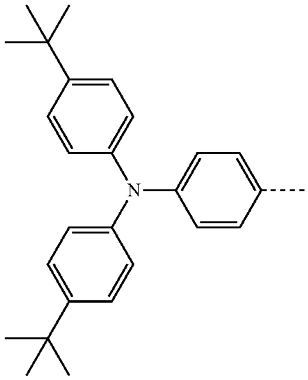
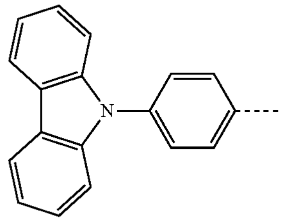
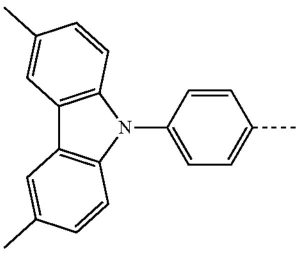
-continued
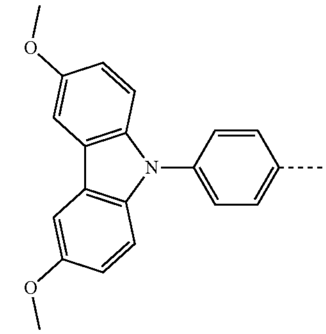
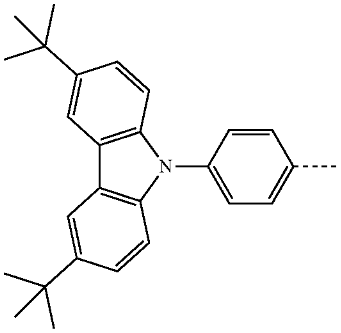
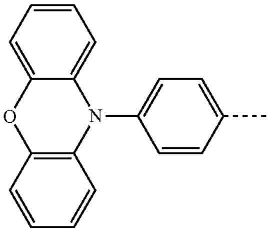
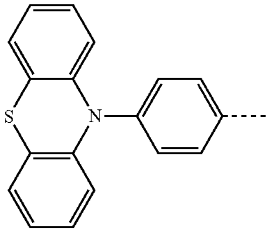
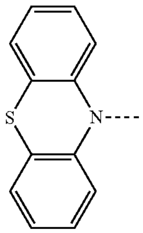
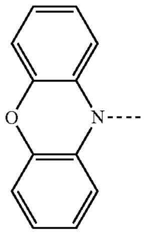
wherein $R_2$ is selected from the group consisting of:
----CN
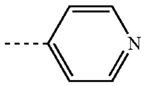
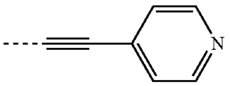

-continued

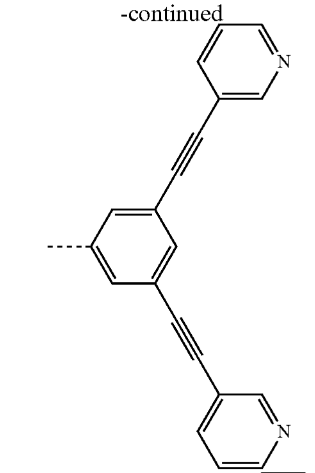

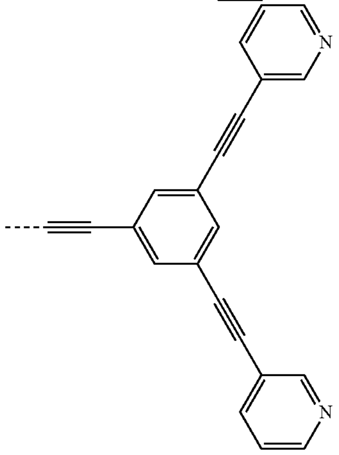

wherein X is selected from the group consisting of —H, —F, and —Cl.

In one example of this embodiment, the fluorescent compound comprises one or more compounds selected from the group consisting of:

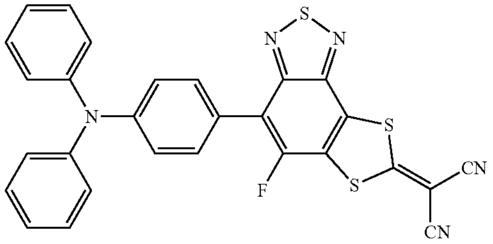

TBSM

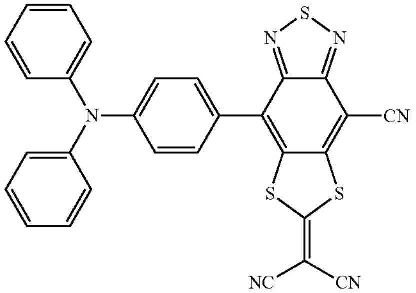

TBSMCN

-continued

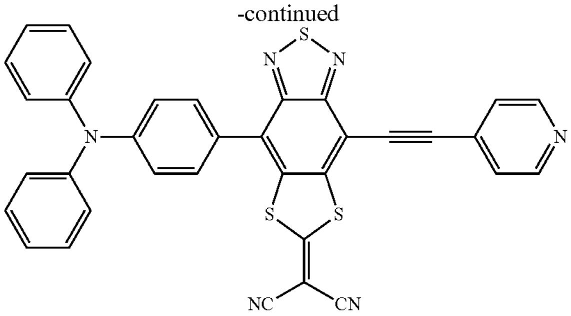

TBSMPy

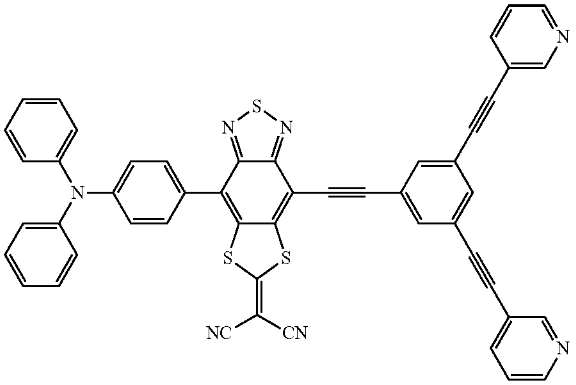

TBSMDPy

In a preferred embodiment of this invention, we provided a new, easy synthesizable acceptor, mono-disulfovalene fused benzodithiazole (BSM), for constructing deep-red/near-infrared luminogens. By varying the donor and the attaching functional groups, deep-red/near-infrared luminogens (650-1300 nm) were easily obtained within five steps, showing excellent luminescence efficiency in aggregated and solid states. Based on this novel donor-acceptor system, lots of applications could be designed including organic light-emitting diode (OLED), chemical sensors, bio-imaging, and photodynamic therapy. As an application example, a triphenylamine (TPA)-BSM based luminogen was prepared which showed bright deep-red emission, excellent two-photo absorption capability, and superior selectivity towards lipid droplets in different levels including living cells, tissues, and live fish embryo.

Application of bio-imaging: Lipid droplets (LDs) are ubiquitous lipid-rich spherical organelles in most cells and organisms. LDs mainly contain triglycerides and cholesterol esters and are enclosed by a phospholipid monolayer with specific proteins. LDs, as dynamic organelles, are involved in many cellular functions, such as lipid metabolism, membrane synthesis and transfer, signal transduction, and protein degradation. Recent studies have shown that LDs are also highly associated with obesity, diabetes, inflammatory disorders and cancer.

Some imaging techniques, such as transmission electron microscopy, Raman microscopy, and immunofluorescence microscopy, have been utilized to visualize LDs. Generally, however, these imaging techniques suffer from complicated procedures, poor cellular permeability, and interfere with cell function. Therefore, the development of effective methods for direct and selective LDs visualization and monitoring in biological samples containing live cells and live tissues is of great importance.

Fluorescence imaging has become an indispensable tool for visualizing the localization and the dynamics of cellular compartments and molecular processes due to its excellent selectivity, remarkable sensitivity and extraordinary temporal/spatial resolution. Compared with one-photon fluorescence imaging, two-photon (TP) fluorescence imaging, which utilizes two near-infrared (NIR) photons as the excitation source, are highly favored in biomedical imaging because of deeper tissue penetration, higher spatial resolution, lower background fluorescence, and lower photodamage and photobleaching.

An abnormality in lipid droplets (LDs) of a cell is a critical biomarker for diseases, such as cancer, diabetes, obesity, fatty liver disease, and inflammatory disorders. The fluorescent compounds described herein can specifically target LDs in live cell, live tissues and live embryos. Also, the fluorescent compounds provide efficient fluorescent probes of the lipid droplets for diagnostic purposes.

The present compounds are lipophilic compounds. Due to the presence of triglycerides and cholesterol esters in LDs, the inherent environment of LDs is also lipophilic. Without being limited to any specific mechanism of action, it is believed that the lipid droplet staining specificity of the present compounds can be attributed to like-like interactions resulting from accumulation of the fluorescent compounds in the hydrophobic lipid droplets. While donor-acceptor (D-A) based organic dyes with increased acceptor ability generally show red-shifted fluorescence, more hydrophobicity and larger two-photon absorption cross section, a balance between hydrophobicity and cell penetrability has previously been difficult to achieve. The present benzothiadiazole-based, D-A compounds described herein can effectively be used for specific LDs visualization in live cells, live tissues and live embryos.

In a second embodiment of the present invention, a method of cellular imaging is provided. The method comprising:

- contacting a target cell with the fluorescent compound described in the first embodiment; and
- identifying a target of interest in the target cell using an imaging method.

In this embodiment, the target of interest comprises lipid droplets. The imaging method can include, for example, fluorescence microscopy or confocal laser scanning microscopy. The fluorescence microscopy can include two-photon fluorescence imaging. The target cell can be a live cell. The target cell can be in live tissue. The target cell can be in live embryos.

Application of optoelectronic devices: Organic electroluminescent devices containing one or more light-emitting layers based on organics such as, e.g., organic light emitting diodes (OLEDs), light emitting electrochemical cells (LECs) and light-emitting transistors gain increasing importance. In particular, OLEDs are promising devices for electronic products such as e.g. screens, displays and illumination devices. In contrast to most electroluminescent devices essentially based on inorganics, organic electroluminescent devices based on organics are often rather flexible and producible in particularly thin layers. The OLED-based screens and displays already available today bear particularly beneficial brilliant colors, contrasts and are comparably efficient with respect to their energy consumption.

A central element of an organic electroluminescent device for generating light is a light-emitting layer placed between an anode and a cathode. When a voltage (and current) is applied to an organic electroluminescent device, holes and electrons are injected from an anode and a cathode, respectively, to the light-emitting layer. Typically, a hole transport layer is located between light-emitting layer and the anode, and an electron transport layer is located between light-emitting layer and the cathode. The different layers are sequentially disposed. Excitons of high energy are then generated by recombination of the holes and the electrons. The decay of such excited states (e.g., singlet states such as S1 and/or triplet states such as T1) to the ground state (S0) desirably leads to light emission.

In order to enable efficient energy transport and emission, an organic electroluminescent device comprises one or more host compounds and one or more emitter compounds as dopants. Challenges when generating organic electroluminescent devices are thus the improvement of the illumination level of the devices (i.e., brightness per current), obtaining a desired light spectrum and achieving suitable (long) lifespans.

Thermally activated delayed fluorescence (TADF) emitters are usually considered as the third-generation electroluminescence (EL) materials for OLEDs. Different from conventional organic molecules, TADF process is as one of the most attractive methods for harvesting both singlet (S1) and triplet (T1) populations in metal-free organic materials because they can achieve a theoretical maximum internal quantum efficiency (IQE) up to 100%.

Because of the high probability of emission quenching, TADF-based emitters are usually employed in an OLED as a doping (guest) into a suitable matrix (host) that should also allow an efficient energy transfer to the emitter via Förster and/or Dexter process.

Most TADF molecules are donor-acceptor (D-A)- or donor-acceptor-donor (D-A-D)-type moieties, which give the bipolar characteristics to a TADF molecule. Several approaches have been studied to improve the host/guest concept in TADF emitters, although the best framework can be emitter-dependent. Recently, was proposed that, if in a host/a guest system based on a TADF dopant, the charge transport is via hole transport in the TADF molecule and simultaneously the electron transport is via the host molecule, therefore the highest occupied molecular orbital (HOMO) levels of the host should be deeper than HOMO levels of TADF.

In a third embodiment of the present invention, an organic electroluminescent device is provided. The method organic electroluminescent device comprising a light-emitting layer comprising:

- at least one host material; and
- at least one thermally activated delayed fluorescence (TADF) material comprising the fluorescent compound described in the first embodiment.

In this embodiment, the organic electroluminescent device is selected from the group consisting of an organic light emitting diode, a light emitting electrochemical cell, and a light-emitting transistor.

The following examples are provided to illustrate further and to facilitate the understanding of the present teachings and are not in any way intended to limit the invention.

EXAMPLES

Example 1—Synthesis, Characterization Representative Compounds

Figure 1:
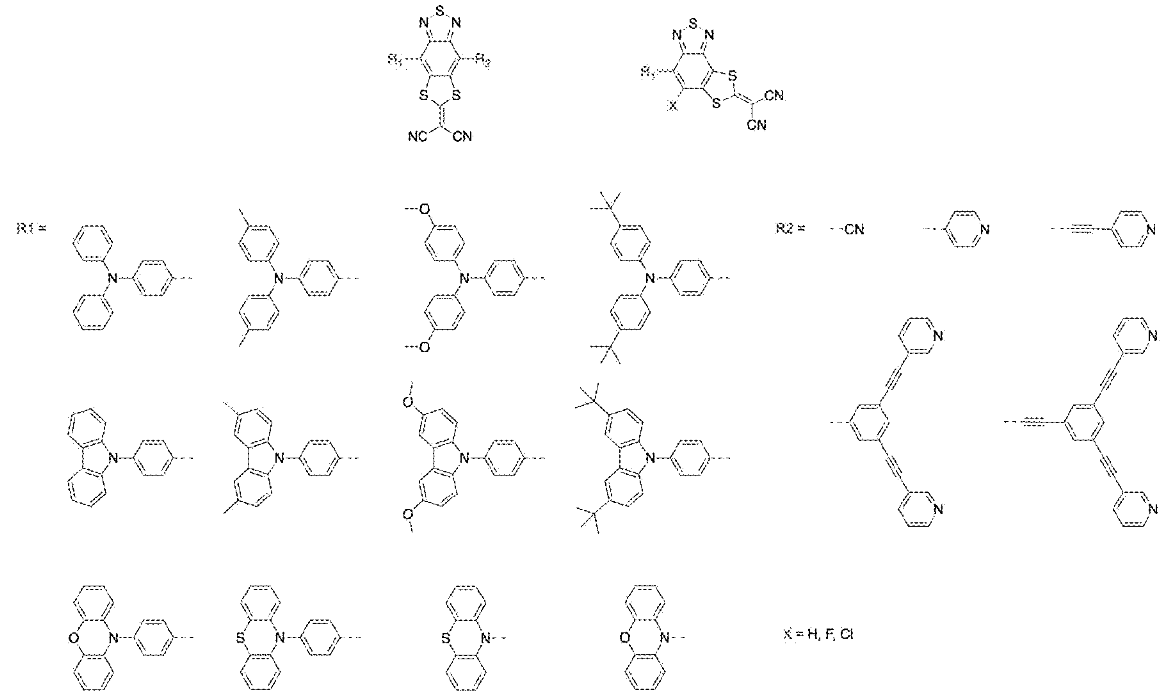
FIG. 1 The proposed structures to be protected.
Figure 2:
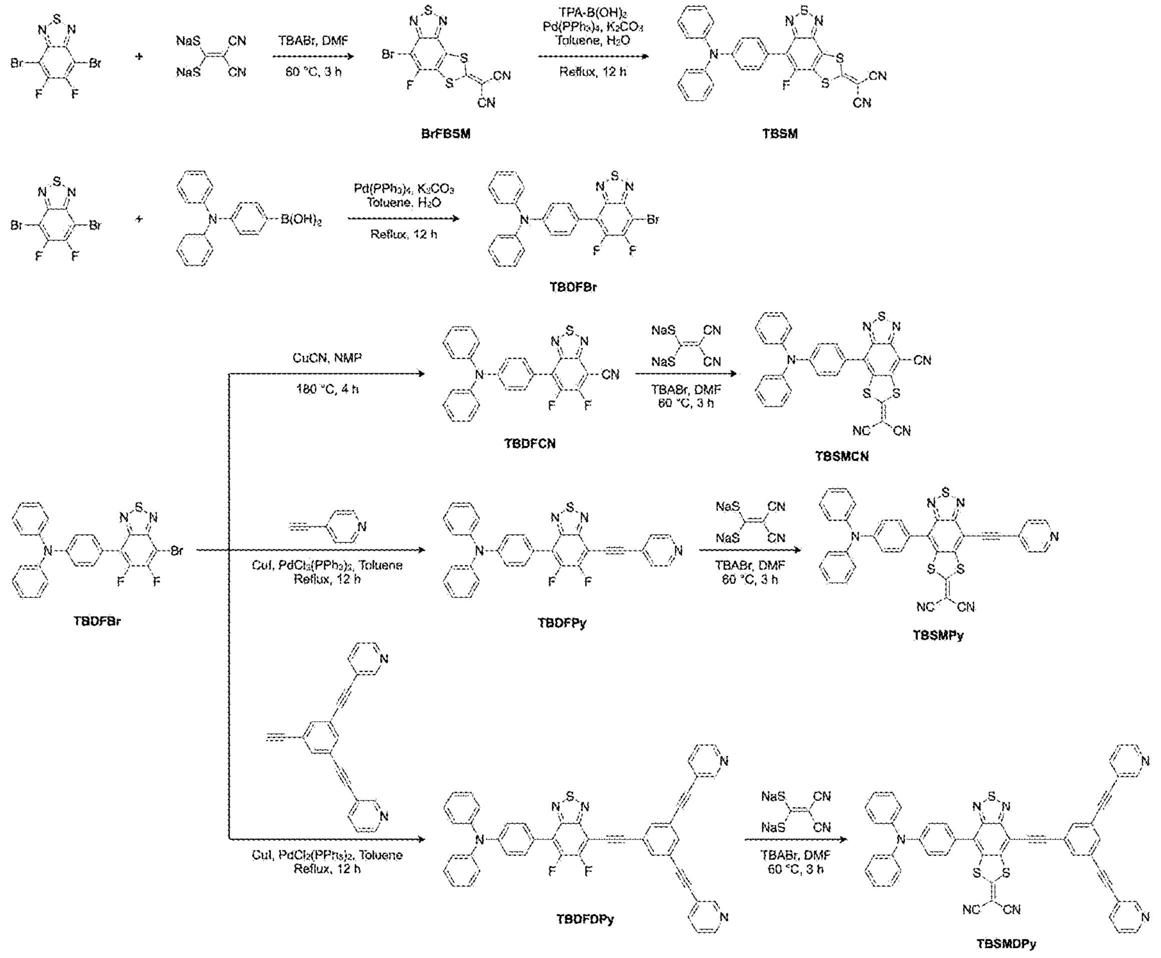
FIG. 2 Synthetic routes to TBSM, TBSMCN, TBSMPy, and TBSMDPy.
Figure 3:
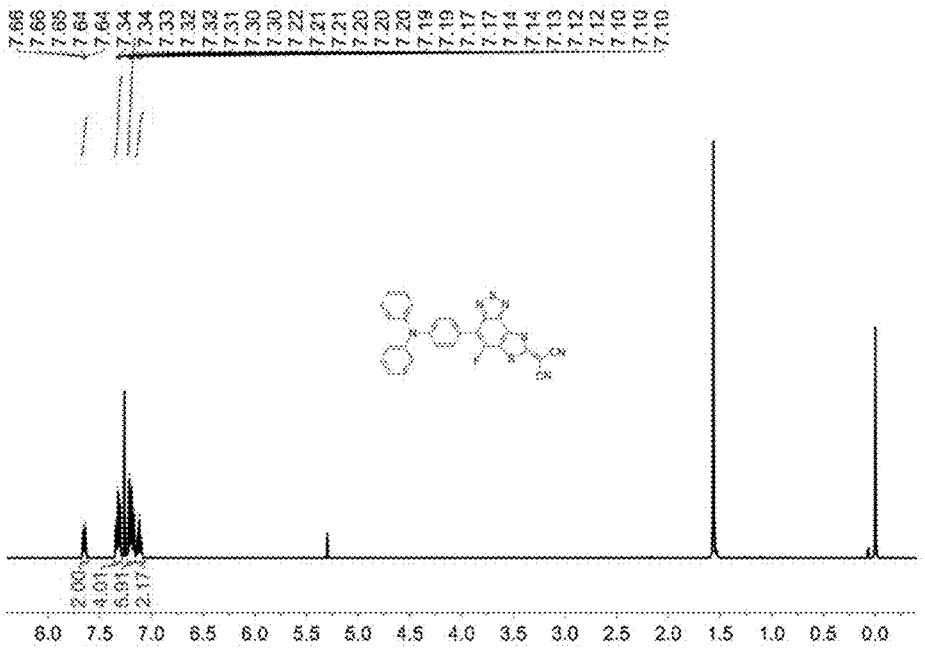
FIG. 3 $^{1}$H NMR of TBSM in $CDCl_3$ at 298K.
Figure 4:
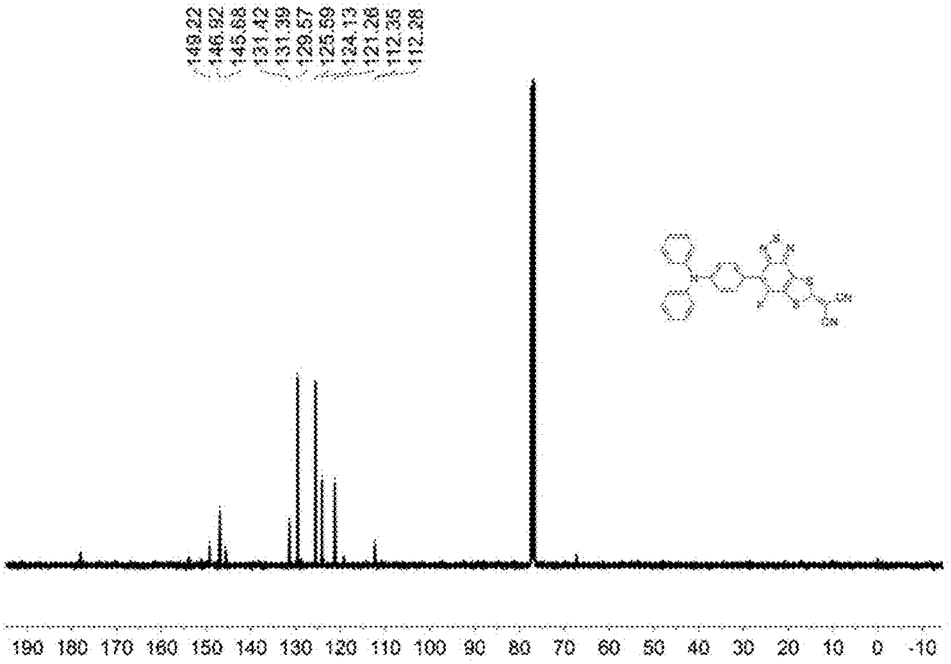
FIG. 4 $^{13}$C NMR of TBSM in $CDCl_3$ at 298K.
Figure 5:
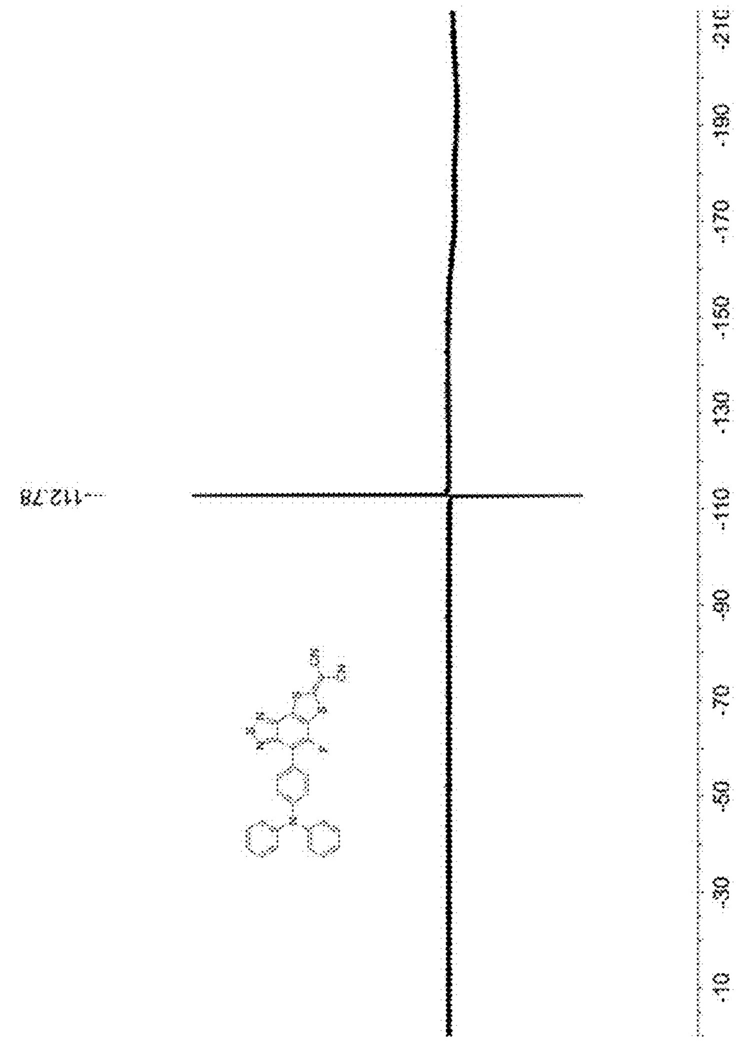
FIG. 5 $^{19}$F NMR of TBSM in $CDCl_3$ at 298K.
Figure 6:
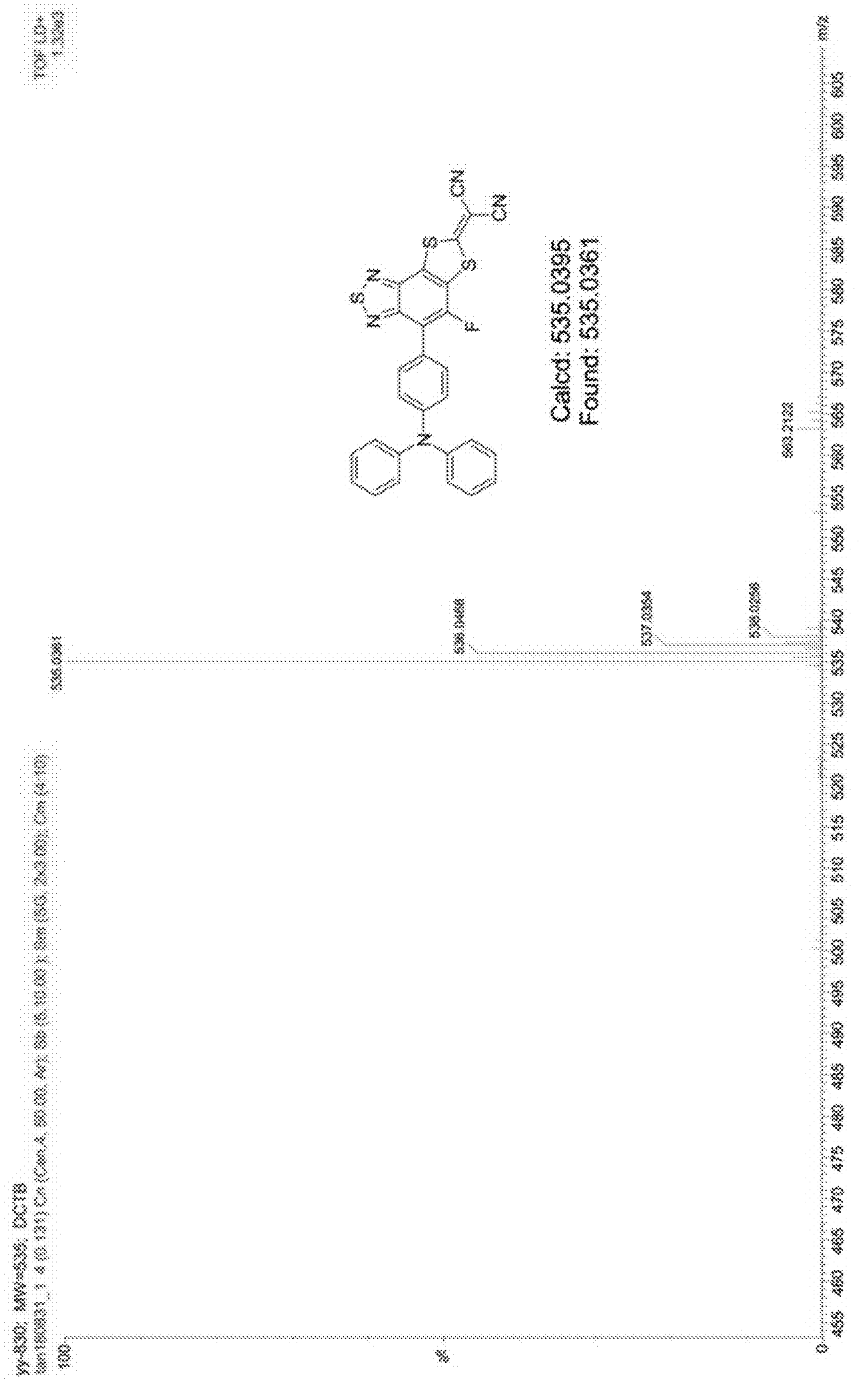
FIG. 6 High resolution mass spectrum of TBSM.
Figure 7:
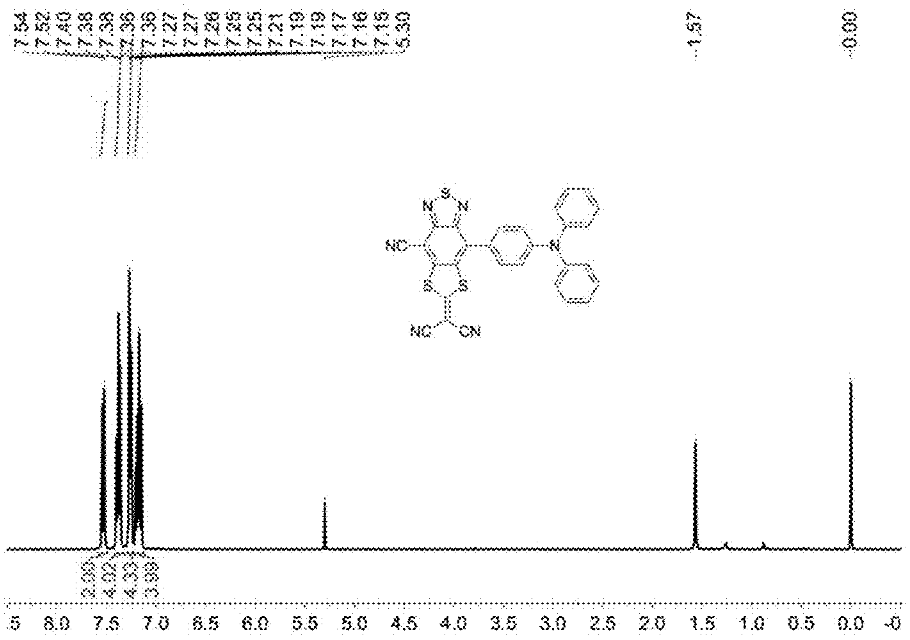
FIG. 7 $^{1}$H NMR of TBSMCN in $CDCl_3$ at 298K.
Figure 8:
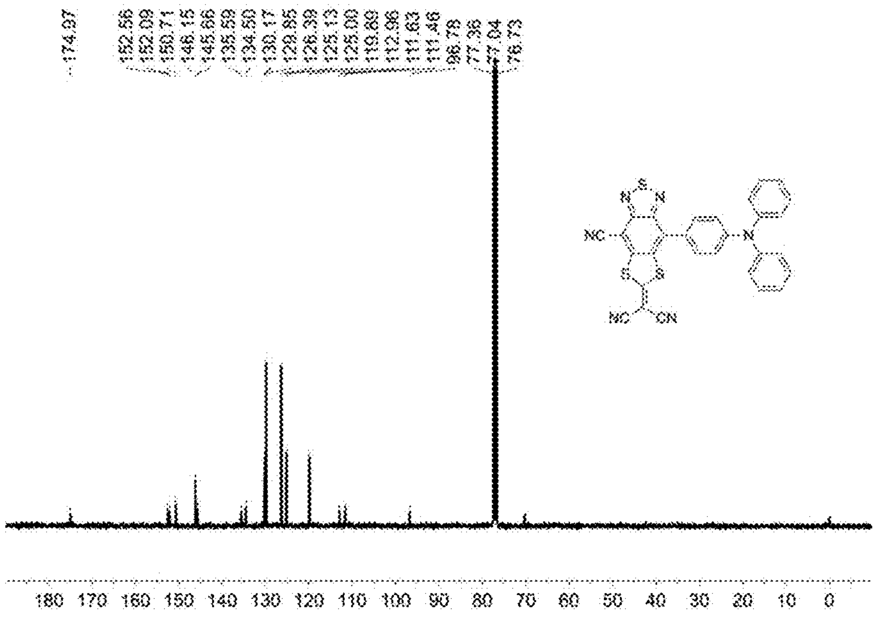
FIG. 8 $^{13}$C NMR of TBSMCN in $CDCl_3$ at 298K.
Figure 9:
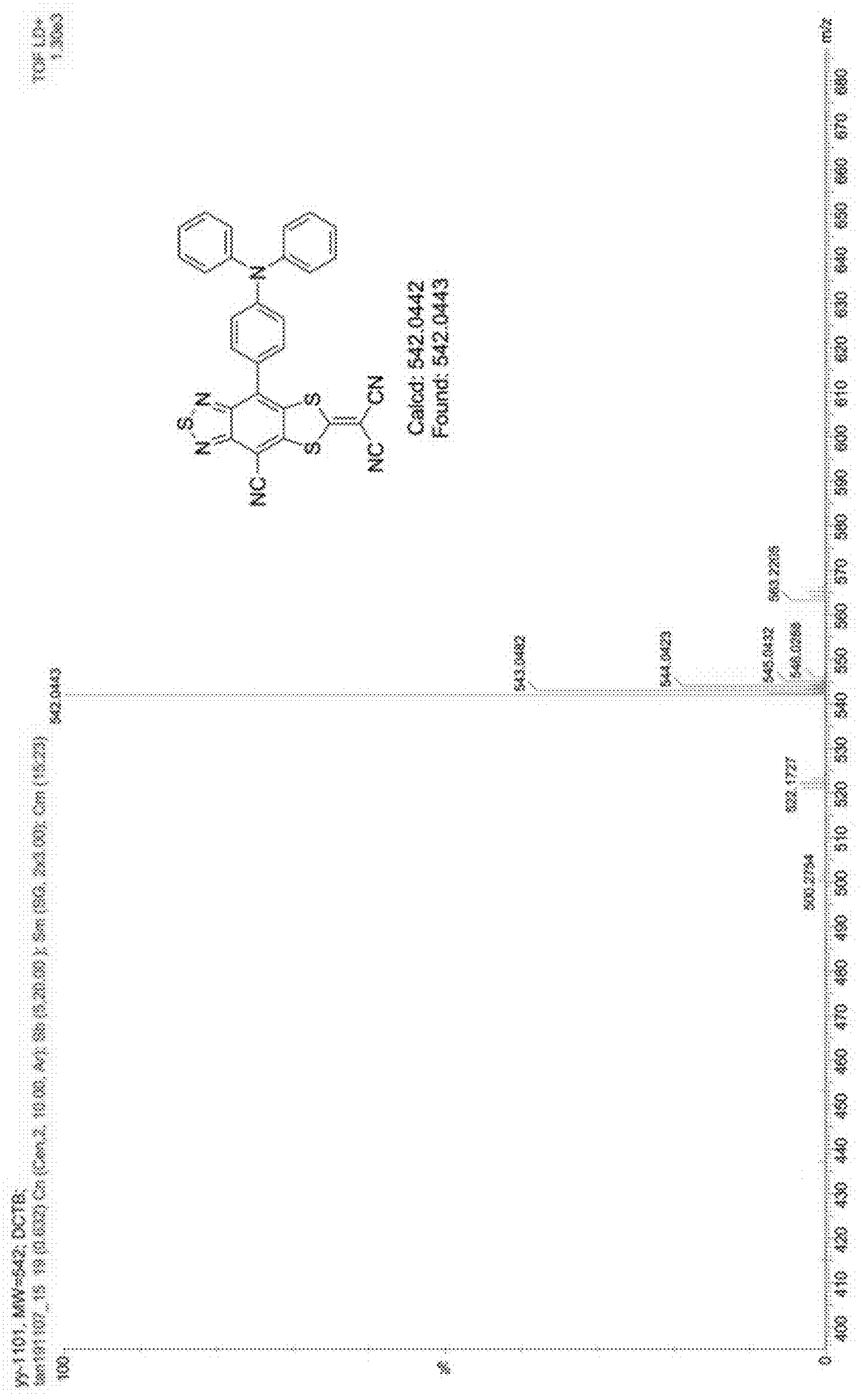
FIG. 9 High resolution mass spectrum of TBSMCN.
Figure 10:
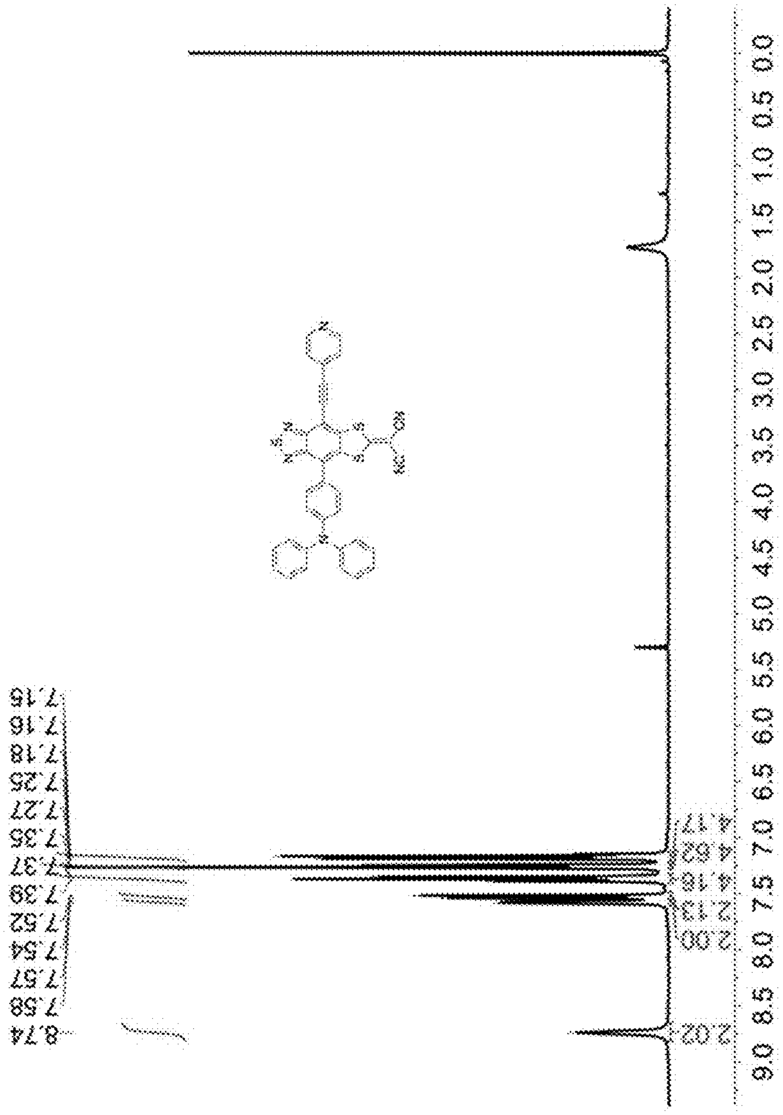
FIG. 10 $^{1}$H NMR of TBSMPy in $CDCl_3$ at 298K.
Figure 11:
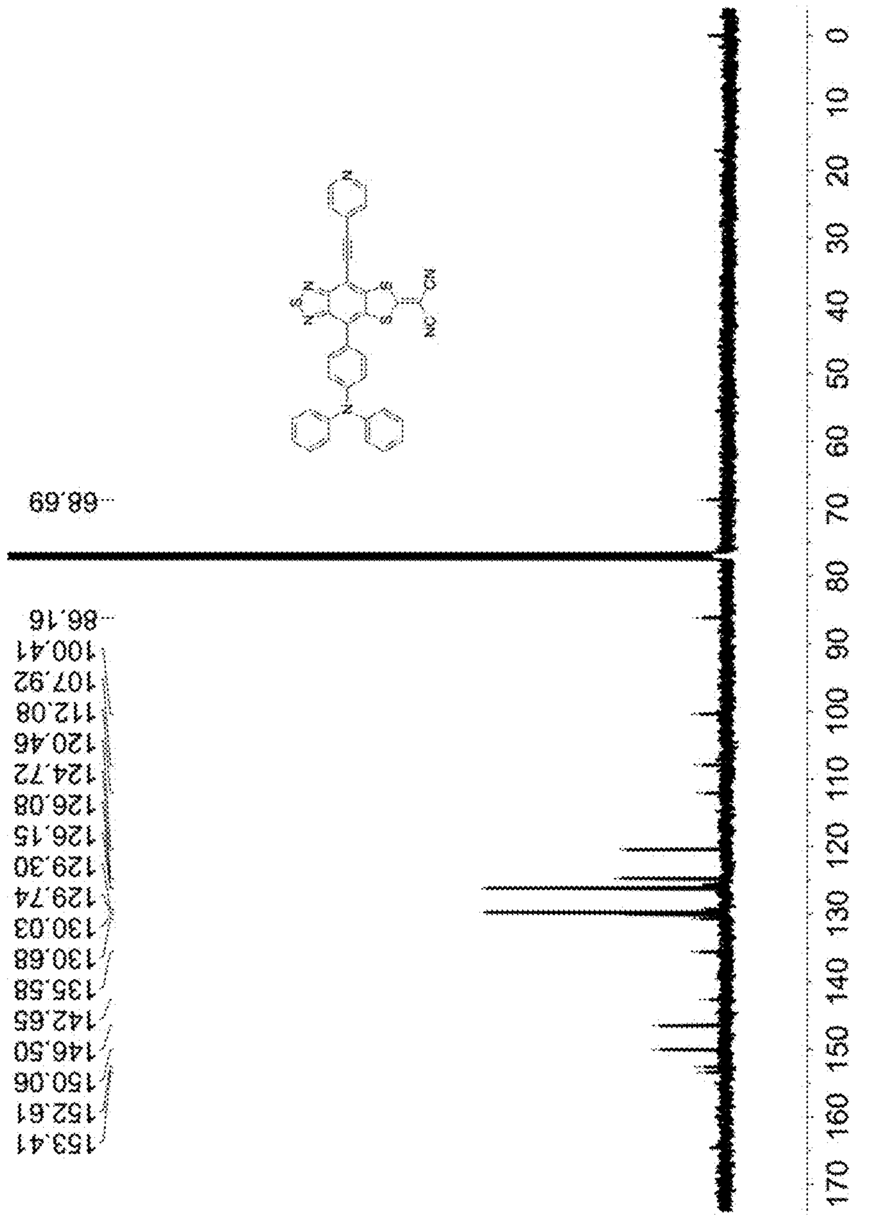
FIG. 11 $^{13}$C NMR of TBSMPy in $CDCl_3$ at 298K.
Figure 12:
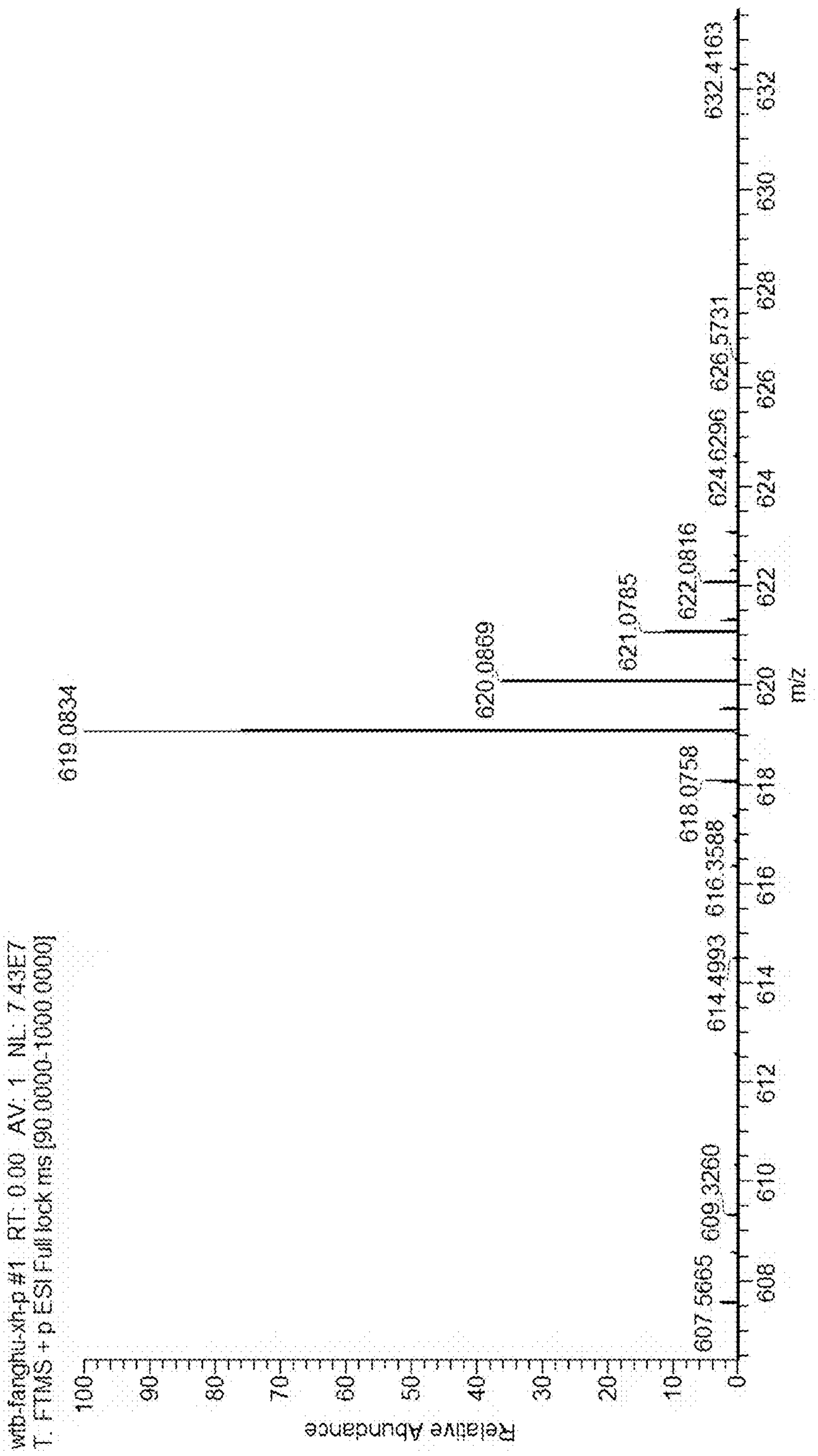
FIG. 12 High resolution mass spectrum of TBSMPy.
Figure 13:
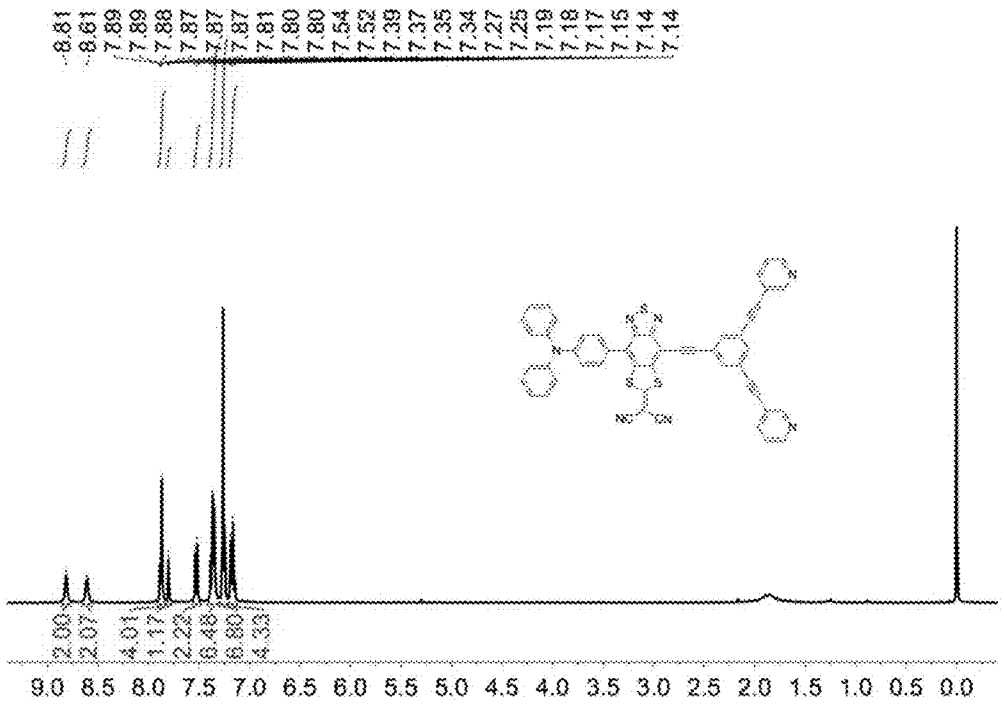
FIG. 13 $^{1}$H NMR of TBSMDPy in $CDCl_3$ at 298K.
Figure 14:
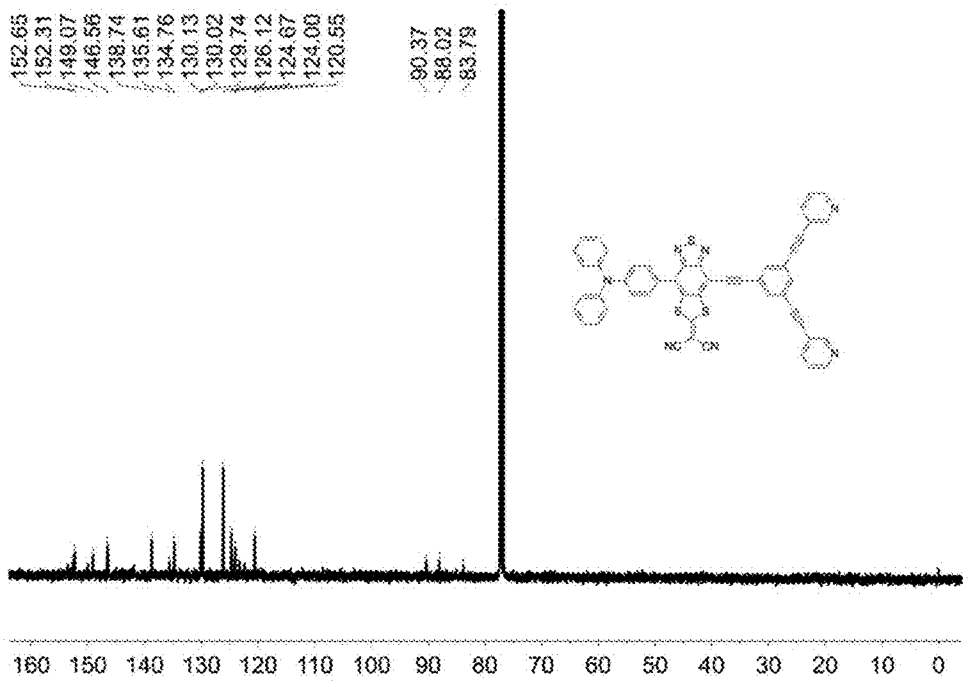
FIG. 14 $^{13}$C NMR of TBSMDPy in $CDCl_3$ at 298K.
Figure 15:
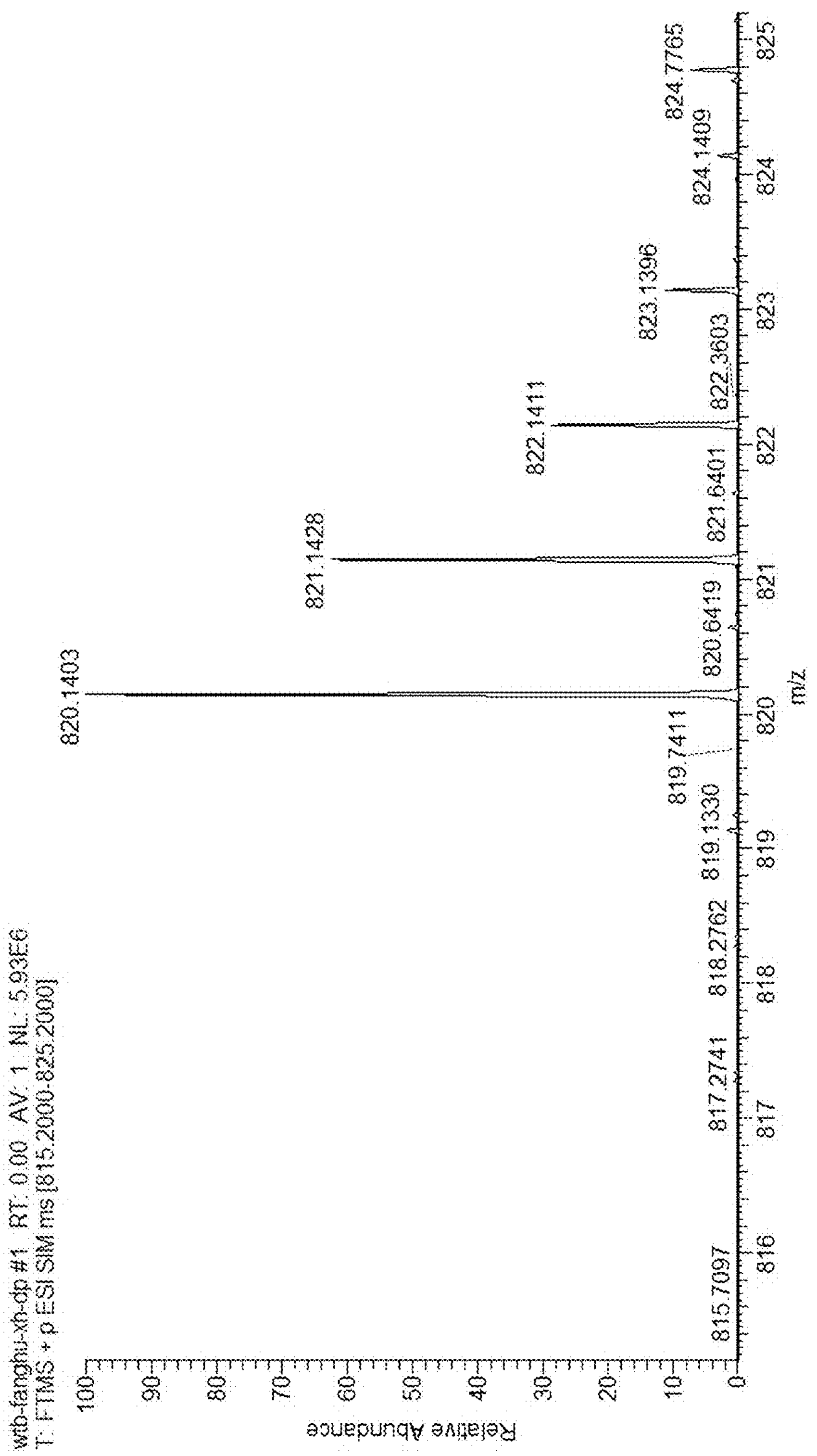
FIG. 15 High resolution mass spectrum of TBSMDPy.

The synthetic routes for the discussed molecules was shown in FIG. 2. In general, Suzuki coupling was utilized to attach the donor moiety (TPA with different R group) onto the benzo[c][1,2,5]thiadiazole acceptor. Further Sonogashira coupling was utilized to attach other functional groups onto the backbone. Finally, the extended acceptor, mono-disulfovalene fused benzodithiazole, was obtained through nucleophilic substitution between obtained structures and sodium 2,2-dicyanoethene-1,1-bis(thiolate). All the new compounds have been characterized by $^{1}$H NMR, $^{13}$C NMR and high-resolution mass spectroscopies with satisfied results.

Example 2—Synthesis of TBSM 4,7-dibromo-5,6-difluorobenzo[c][1,2,5]thiadiazole (165 mg, 0.5 mmol), di(alkalimercapto)methylenemalononitriles (93 mg, 0.5 mmol), and tetra-n-butylammonium bromide (TBABr) (200 mg, 0.6 mmol) were added into a 100 mL two-necked round-bottom flask with 20 mL of DMF. The mixture was then heated to 80° C. for 3 h. After cooled to room temperature, the mixture was poured to water and extracted with DCM. The organic phase was washed with saturated NaCl solution and dried with anhydrous magnesium sulfate. After filtration and solvent evaporation, the residue was purified by silica-gel column chromatography using DCM/hexane mixture (1/1, v/v) as eluent. Yellow solid of BrFBSM was obtained in 36.7% yield (68 mg). MS (MALDI-TOF): m/z 371.8469 ($M^+$, calcd 371.2204). BrFBSM (300 mg, 0.8 mmol), 4-(diphenylamino)phenyl) boronic acid (TPA-B(OH)$_2$ (290 mg, 1 mmol), $Cs_2CO_3$ (890 mg, 6.5 mmol) and $Pd(PPh_3)_4$ (12 mg, 0.08 mmol) were added into a 100 mL two-necked round-bottom flask with 20 mL of distilled toluene and 2 mL water. The mixture was then heated under reflux under nitrogen for 12 h. After cooled to room temperature, the mixture was poured to water and extracted with DCM. The organic phase was washed with saturated NaCl solution and dried with anhydrous magnesium sulfate. After filtration and solvent evaporation, the residue was purified by silica-gel column chromatography using DCM/hexane mixture (2/1, v/v) as eluent. Red solid of TBSM was obtained in 57.8% yield (250 mg). $^{1}$H NMR (400 MHz, $CDCl_3$, 298 K), δ (ppm): 7.66-7.64 (d, 2H, J=8 Hz), 7.34-7.30 (t, 4H, J=8 Hz), 7.22-7.17 (m, 6H), 7.14-7.10 (t, 2H, J=8 Hz). $^{13}$C NMR (100 MHz, $CDCl_3$, 298 K), δ (ppm): 149.22, 146.92, 145.68, 131.42, 131.39, 129.57, 124.13, 121.26, 112.35, 112.28. $^{19}$F NMR (376 MHz, $CDCl_3$, 298 K), (δ (ppm): −112.78. MS (MALDI-TOF): m/z 535.0361 ($M^+$, calcd 535.0395).

Example 3—Synthesis of TBDFBr 4,7-dibromo-5,6-difluorobenzo[c][1,2,5]thiadiazole (3 g, 9 mmol), TPA-B(OH)$_2$ (2.64 g, 9 mmol), $Pd(PPh_3)_4$ (1.05 g, 0.9 mmol), and $K_2CO_3$ (9.9 g, 72 mmol) were added into a 250 mL two-necked round-bottom flask with 100 mL of distilled toluene and 20 mL water. The mixture was then heated under reflux under nitrogen for 12 h. After cooled to room temperature, the mixture was poured to water and extracted with DCM. The organic phase was washed with saturated NaCl solution and dried with anhydrous magnesium sulfate. After filtration and solvent evaporation, the residue was purified by silica-gel column chromatography using DCM/hexane mixture (1/1, v/v) as eluent. Yellow solid of TBDFBr was obtained in 47.3% yield (2.1 g).

Example 4—Synthesis of TBSMCN

TBDFBr (660 mg, 1.3 mmol) and CuCN (180 mg, 2 mmol) were dissolved in 15 mL methylpyrrolidone (NMP) and the mixture was heated up to 180'C for 4 h. After cooled to room temperature, the reaction was quenched by adding ammonium solution and the mixture was then poured into water and extracted with DCM. The organic phase was washed with saturated NaCl solution and dried with anhydrous magnesium sulfate. After filtration and solvent evaporation, the residue was purified by silica-gel column chromatography using DCM/hexane mixture (2/1, v/v) as eluent. Red solid of TBDFCN was obtained in 45.5% yield (260 mg). TBDFCN (150 mg, 0.22 mmol), di(alkalimercapto) methylenemalononitriles (96 mg, 0.5 mmol), and tetra-n-butylammonium bromide (TBABr) (500 mg, 1.5 mmol) were added into a 50 mL two-necked round-bottom flask with 15 mL of DMF. The mixture was then heated to 80° C. for 3 h. After cooled to room temperature, the mixture was poured to water and extracted with DCM. The organic phase was washed with saturated NaCl solution and dried with anhydrous magnesium sulfate. After filtration and solvent evaporation, the residue was purified by silica-gel column chromatography using DCM/hexane mixture (2/1, v/v) as eluent. Dark green solid of TBSMCN was obtained in 65.2% yield (120 mg). $^{1}$H NMR (400 MHz, $CDCl_3$, 298 K), δ (ppm): 7.56-7.54 (d, 2H, J=8 Hz), 7.42-7.38 (t, 4H, J=8 Hz), 7.29-7.27 (m, 6H), 7.23-7.17 (m, 8H). $^{13}$C NMR (100 MHz, $CDCl_3$, 298 K), δ (ppm): 152.56, 150.71, 146.15, 134.50, 130.16, 129.84, 126.39, 125.12, 124.99, 119.88, 111.44. MS (MALDI-TOF): m/z 542.0442 ($M^+$, calcd 542.0443).

Example 5—Synthesis of TBSMPy

TBDFBr (1 g, 2 mmol), 4-ethynylpyridine (400 mg, 3.88 mmol), CuI (50 mg, 0.26 mmol), and $PdCl_2(PPh_3)_2$ (200 mg, 0.28 mmol) were added into a 100 mL two-necked round-bottom flask with 40 mL of distilled toluene. The mixture was then heated under reflux under nitrogen for 12 h. After cooled to room temperature, the mixture was poured to water and extracted with DCM. The organic phase was washed with saturated NaCl solution and dried with anhydrous magnesium sulfate. After filtration and solvent evaporation, the residue was purified by silica-gel column chromatography using DCM/hexane mixture (2/1, v/v) as eluent. Red solid of TBDFPy was obtained in 85.9% yield (900 mg). TBDFPy (50 mg, 0.1 mmol), di(alkalimercapto)methylenemalononitriles (27 mg, 0.15 mmol), and tetra-n-butylammonium bromide (TBABr) (145 mg, 0.45 mmol) were added into a 25 mL two-necked round-bottom flask with 10 mL of DMF. The mixture was then heated to 80° C. for 3 h. After cooled to room temperature, the mixture was poured to water and extracted with DCM. The organic phase was washed with saturated NaCl solution and dried with anhydrous magnesium sulfate. After filtration and solvent evaporation, the residue was purified by silica-gel column chromatography using DCM/hexane mixture (2/1, v/v) as eluent. Dark purple solid of TBSMPy was obtained in 32.7% yield (20 mg). $^{1}$H NMR (400 MHz, $CDCl_3$, 298 K), δ (ppm): 8.81 (s, 2H), 8.61 (s, 2H), 7.89-7.87 (m, 4H), 7.81-7.80 (t, 1H, J=2 Hz), 7.54-7.52 (d, 2H, J=8 Hz), 7.39-7.34 (m, 6H), 7.27-7.25 (d, 6H, J=8 Hz), 7.19-7.14 (m, 4H). $^{13}$C NMR (100 MHz, $CDCl_3$, 298 K), δ (ppm): 152.65, 152.31, 149.07, 146.56, 138.74, 135.61, 134.76, 130.13, 130.02, 129.74, 126.12, 124.67, 124.00, 120.55, 90.37, 88.02, 83.79. MS (MALDI-TOF): m/z 820.1403 ($M^+$, calcd 820.1334).

Example 6—Synthesis of TBSMDPy

TBDFBr (486 mg, 1 mmol), 3,3'-((5-ethynyl-1,3-phenylene)bis(ethyne-2,1-diyl))dipyridine (200 mg, 0.65 mmol), CuI (12 mg, 0.065 mmol), and $PdCl_2(PPh_3)_2$ (75 mg, 0.065 mmol) were added into a 50 mL two-necked round-bottom flask with 20 mL of distilled toluene. The mixture was then heated under reflux under nitrogen for 12 h. After cooled to room temperature, the mixture was poured to water and extracted with DCM. The organic phase was washed with saturated NaCl solution and dried with anhydrous magnesium sulfate. After filtration and solvent evaporation, the residue was purified by silica-gel column chromatography using DCM/hexane mixture (2/1, v/v) as eluent. Red solid of TBDFDPy was obtained in 41.0% yield (300 mg). TBDFDPy (80 mg, 0.11 mmol), di(alkalimercapto) methylenemalononitriles (31 mg, 0.17 mmol), and tetra-n-butylammonium bromide (TBABr) (161 mg, 0.5 mmol) were added into a 25 mL two-necked round-bottom flask with 10 mL of DMF. The mixture was then heated to 80° C. for 3 h. After cooled to room temperature, the mixture was poured to water and extracted with DCM. The organic phase was washed with saturated NaCl solution and dried with anhydrous magnesium sulfate. After filtration and solvent evaporation, the residue was purified by silica-gel column chromatography using DCM/hexane mixture (2/1, v/v) as eluent. Dark purple solid of TBSMDPy was obtained in 33.3% yield (30 mg). $^1$H NMR (400 MHz, $CDCl_3$, 298 K), δ (ppm): 8.74 (s, 2H), 7.58-7.57 (d, 2H, J=4 Hz), 7.54-7.52 (d, 2H, J=8 Hz), 7.39-7.35 (t, 4H, J=8 Hz), 7.27-7.25 (d, 4H, J=8 Hz), 7.18-7.15 (t, 4H, J=6 Hz). $^{13}$C NMR (100 MHz, $CDCl_3$, 298 K), δ (ppm): 153.41, 152.61, 150.06, 146.50, 142.65, 135.58, 130.68, 130.03, 129.74, 129.30, 126.15, 126.08, 124.72, 120.46, 112.08, 107.92, 100.41, 86.16. MS (MALDI-TOF): m/z 619.0834 ($M^+$, calcd 619.0755).

Example 7—Photophysical Properties of TBSM

Figure 16B:
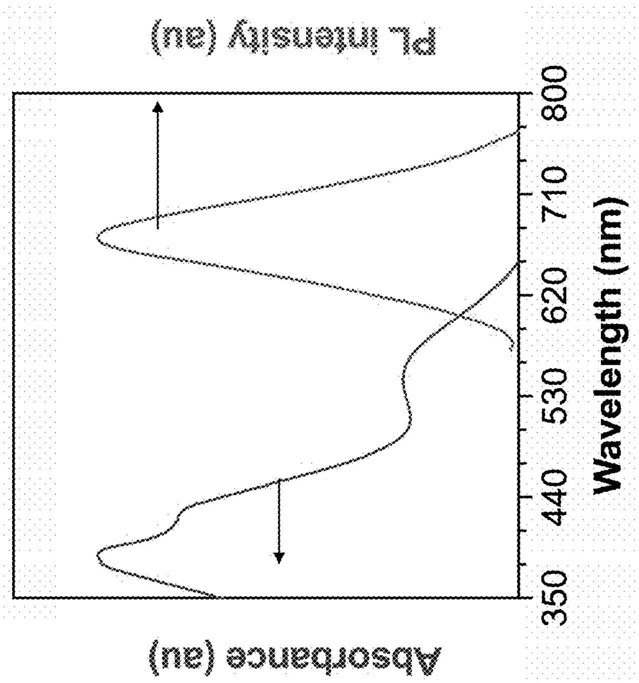
FIG. 16A Normalized absorption and PL spectra of TBSM in THF solution (c=$10^{-5}$ M) and FIG. 16B Normalized absorption and PL spectra of TBSM in solid state. $\lambda_{ex}$=460 nm.
Figure 16A:
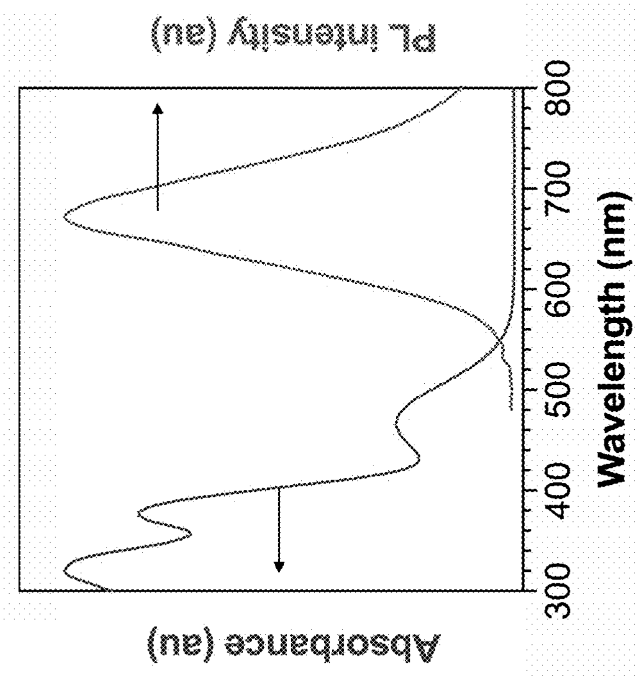

The photophysical properties of TBSM were first examined. The tetrahydrofuran (THF) solution of TBSM exhibited three absorption peaks at 315 nm, 370 nm and 460 nm, in which the first one could be assigned to a π-π* absorption, the second one arose from the BSM moiety, and the last one was from the intramolecular charge transfer (ICT) absorption. TBSM gave a much brighter red emission in toluene solution with an emission wavelength at 605 nm and a QY of 67.9%. While in THF solution, the emission wavelength red-shifted to 669 nm with a QY of 4.1%. The varied luminescence behavior of TBSM in different solvents suggests the existence of TICT effect (FIG. 16A and FIG. 16B).

Figure 17A:
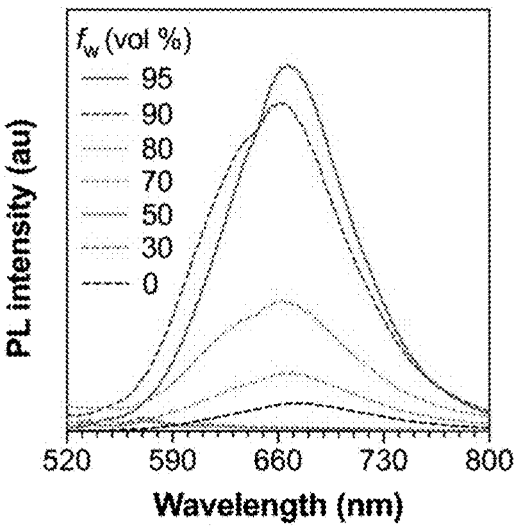
FIG. 17A PL spectra of TBSM in water/THF mixtures with different water fractions ($f_w$)
Figure 17B:
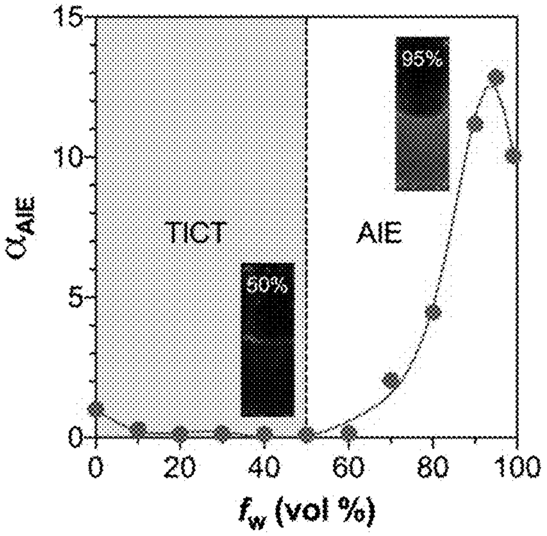
FIG. 17B Plots of relative PL intensity ($\alpha_{AIE}=I/I_0$, $I_0$=PL intensity in pure THF at 672 nm) vs $f_w$. c=10 μM, $\lambda_{ex}$=460 nm. Insert: the fluorescence pictures of the mixture with $f_w$=50% and 95%.

We then investigated the luminescence behavior of TBSM in the mixture of THF and water to see whether it is AIE-active. When adding water into the THF solution, the photoluminescence (PL) intensity decreased with the water fraction ($f_w$) in a range of 0-50%. In this case, the TICT effect dominated the photophysical process and reduced the emission intensity. When the $f_w$ exceeded 50%, the TBSM molecule began to aggregate and made the local microenvironment less polar. Therefore, the conformation rigidification became dominated and reversed the PL intensity from weak to strong. Thus, TBSM exhibits typical AIE property (FIG. 17A and FIG. 17B).

Example 8—Single Crystal Structure

Figure 18A:
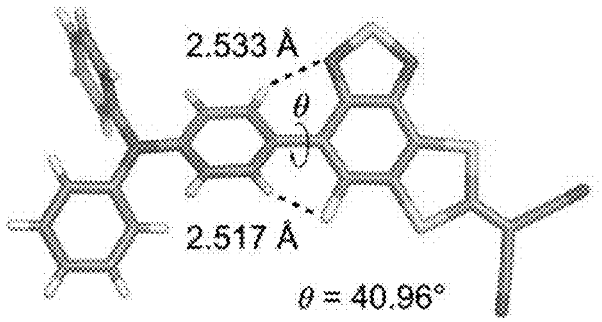
FIG. 18A Single crystal structure of TBSM.
Figure 18B:
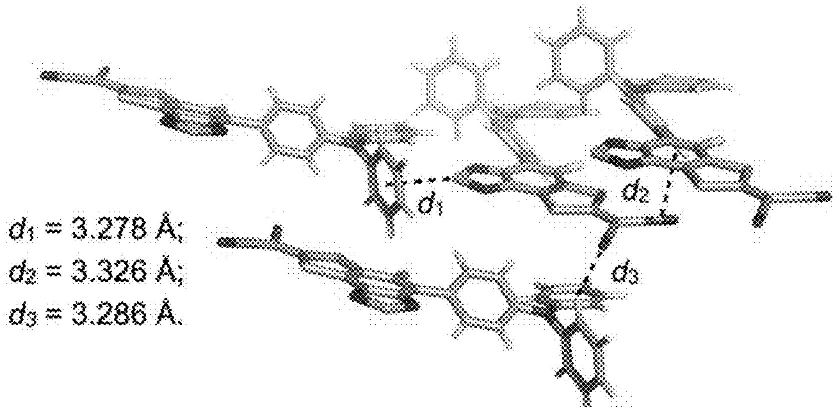
FIG. 18B D-A interactions and π-π interactions in crystal of TBSM.
Figure 18C:
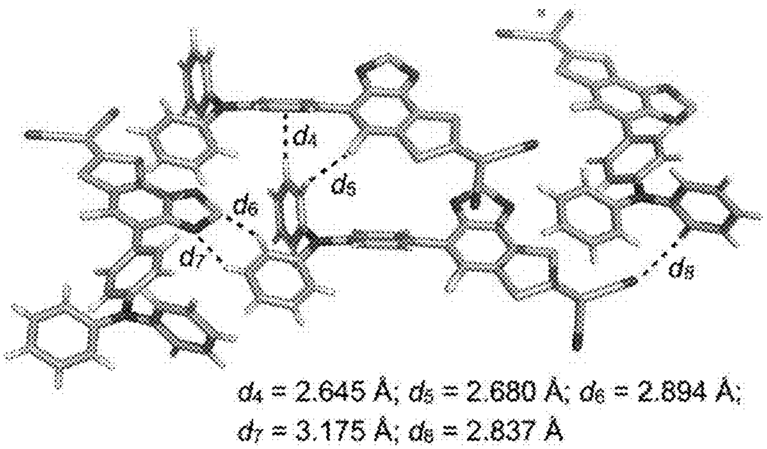
FIG. 18C Intermolecular weak interactions in crystal of TBSM.

To gain an insight to the details of the photophyscial properties of TBSM, we analyzed its crystal structure. TBSM molecules also show bright emission in the solid state since the locked nonplanar conformation can avoid the strong intermolecular π-π interactions. Indeed, no strong intermolecular π-π stacking has been observed in the crystal packing of TBSM. However, multiple intermolecular non-covalent interactions such as S . . . π, C≡N . . . π, C—H . . . N, C—H . . . S, and intermolecular hydrogen bonding interactions were observed which helps lock the solid-state molecular motion. As a result, the solid of TBSM exhibit much strong deep red emission at a wavelength of 670 nm with a quantum yield of 13% (FIG. 18A, FIG. 18B and FIG. 180).

Example 9—Bio-Imaging

Figure 19:
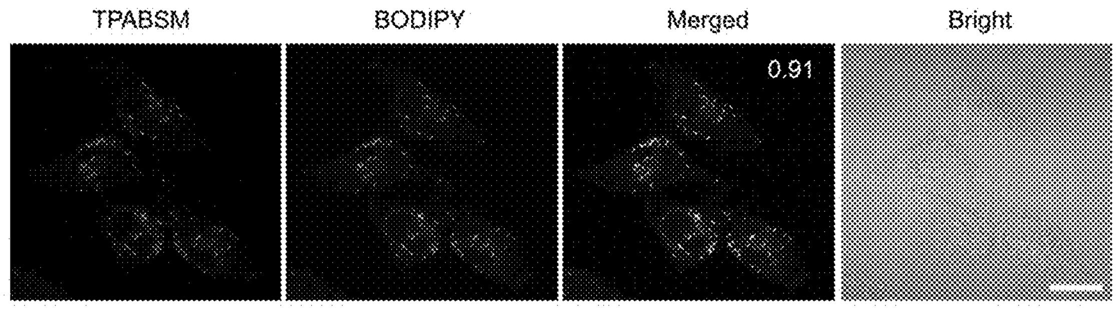
FIG. 19 Confocal fluorescent images of live HeLa cell stained with 2 μM TBSM (1 h) and 1 μg/mL BODIPY (1 h). TBSM: $\lambda_{ex}$=488 nm, $\lambda_{em}$=550-650 nm; BODIPY: $\lambda_{ex}$=488 nm, $\lambda_{em}$=490-535 nm. Scale bar=20 μm. The number on the figure is colocalization coefficient.

TBSM is a superior liposoluble luminescent molecule, and the fluorine is a commonly used atom to improve the lipophilicity of drug molecules, which thus inspired us to explore the possibility of TBSM as a dye for lipid droplets (LDs) imaging. Incubated with 2 μM TBSM for 1 h, the A549 and Hela cells were successfully stained and emitted around 640 nm, suggesting a fast permeability of TBSM for living cells. To confirm the specificity of the TBSM for LDs imaging, the co-localization experiments were then carried out by incubating Hela cells with TBSM and BODIPY 493/503, a commercial dye for LDs. The results showed that TBSM stains LDs specifically with a co-localization coefficient of 0.91 (FIG. 19).

Figure 20:
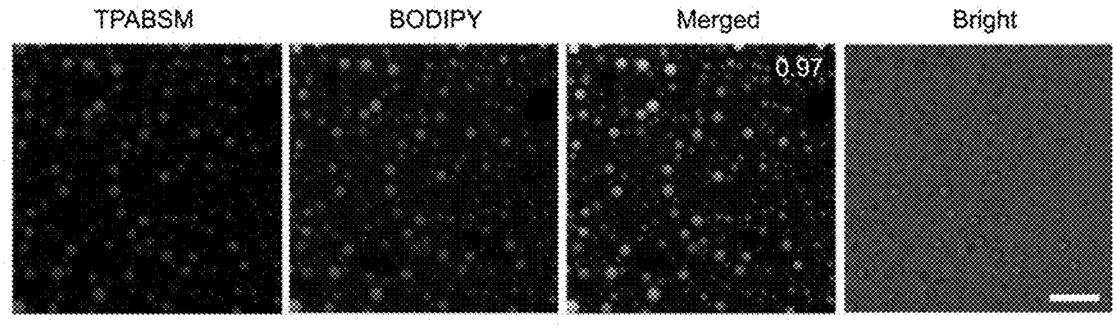
FIG. 20 Co-stained ex vivo confocal one-photon ($\lambda_{ex}$=488 nm) images TBSM (2 μM, 1 h) and BODIPY (2 μM, 1 h) in high-fat feeding mice liver tissue. TBSM: $\lambda_{ex}$=488 nm, $\lambda_{em}$=550-650 nm; BODIPY: $\mu_{ex}$=488 nm, $\lambda_{em}$=490-535 nm. Scale bar: 10 μm. The number on the picture is colocalization coefficient.
Figure 21A:
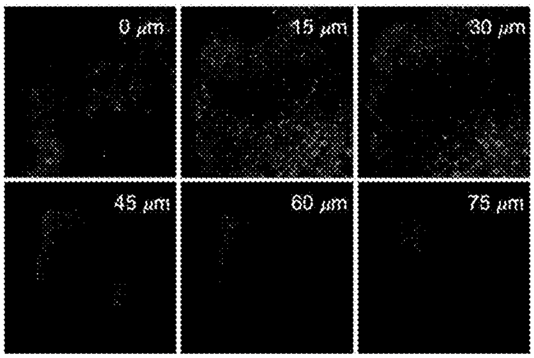
FIG. 21A Two-photon ($\lambda_{ex}$=880 nm) images of and FIG. 21C one-photon ($\lambda_{ex}$=488 nm) images of high-fat feeding mice liver tissue stained with TBSM (4 μM, 1 h) at different penetration depths. $\lambda_{em}$=550-650 nm FIG. 21B Reconstructed 3D two-photon images.
Figure 21B:
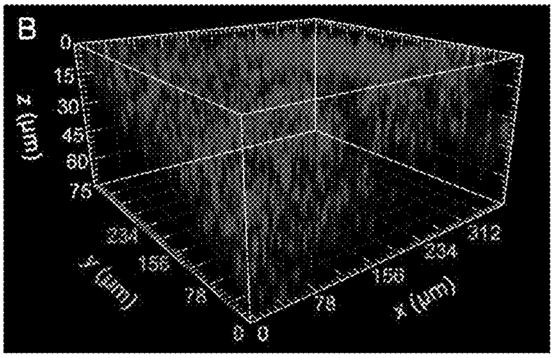
FIG. 21D Reconstructed 3D one-photon images. Scale bar: 40 μm in FIG. 21A and 20 μm in FIG. 21C. Two photon penetration depth: 72 μm, One photon penetration depth: 15 μm.
Figure 21C:
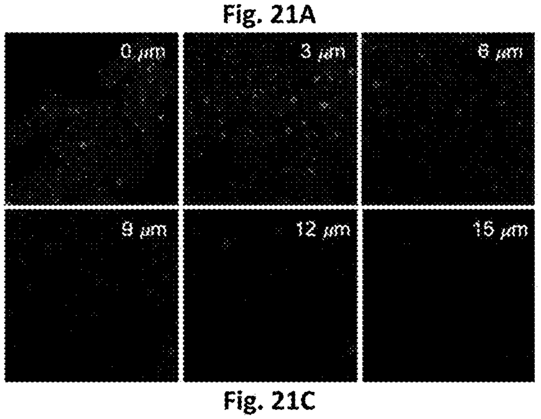
Figure 21D:
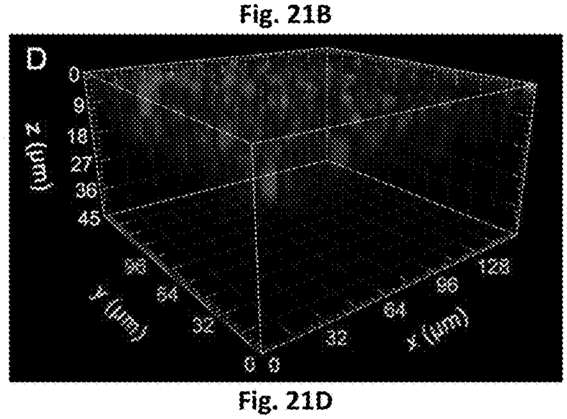

Apart from living cells, the LDs of liver tissues of mice can also be clearly stained by TBSM, suggesting the high penetration depth. By comparing the images of normal and high-fat feeding mice liver tissues, apparent deep-red emission was observed in high-fat feeding mice liver tissue. Furthermore, co-staining experiments with BODIPY shows a high co-localization coefficient (0.97), indicating the potential of TBSM for the specific tissue or in vivo LDs imaging (FIG. 20).

In comparison with luminogens with one-photon excitation, the excitation wavelength of two-photon luminogens can be extended to a deep red region or even near-infrared region, which can successfully overcome the drawbacks of short wavelength excitation. The two-photon image shows much higher imaging contrast for liver tissue of high-fat feeding mice. Besides, 3D one-photon and two-photon fluorescent images along different visual directions were reconstructed by combining the images at different depth (FIG. 21A, FIG. 21B, FIG. 21C and FIG. 21D). The results indicate that the two-photon imaging could reach a depth of 72 μm with superior resolution while the one-photon imaging could only reach a depth of 15 μm with lower resolution. One-photon cell imaging experiments were performed by confocal laser scanning microscopy (CLSM).

Figure 22:
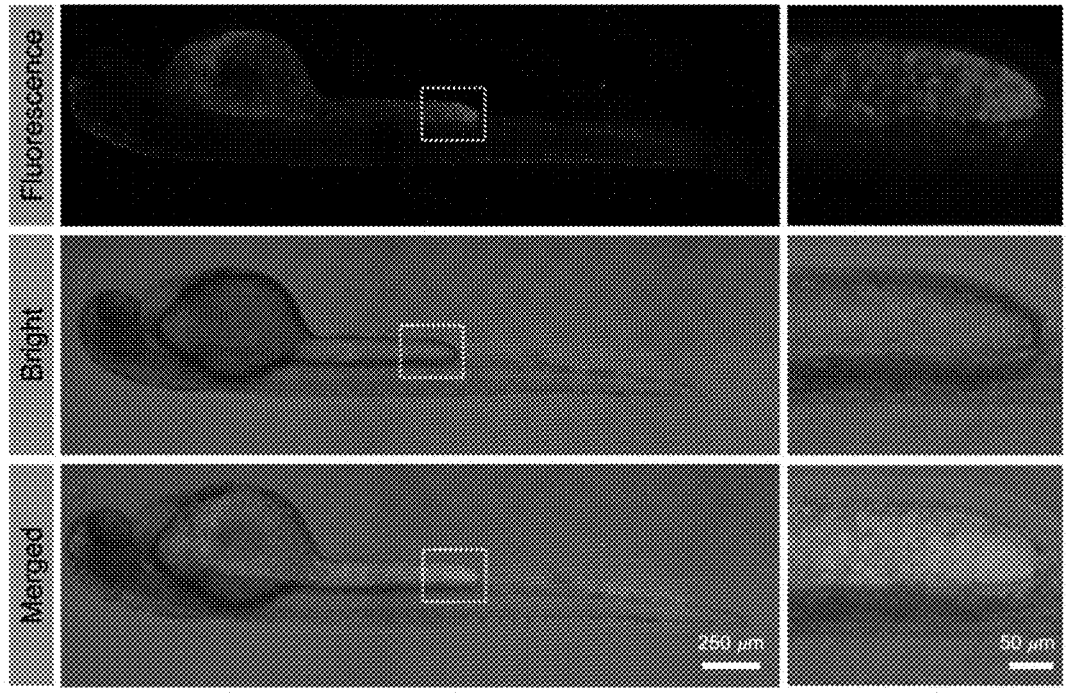
FIG. 22 In vivo zebrafish embryo imaging stained with TBSM (1 μM, 1 h), $\lambda_{ex}$=488 nm, $\lambda_{em}$=550-650 nm. The right is the enlarged part of white frame in the left.

The excellent performance of TBSM for LDs imaging suggests it's potential in imaging the LDs in vivo. Yolk sac as a neutral lipid and polar phospholipids storage organ provides energy for the upgrowth of zebrafish. Intense red fluorescence signals originating from the yolk sac in 3-day-old zebrafish embryos were observed after stained with TBSM for 30 min (FIG. 22). The enlarged parts exhibited more explicit staining images, showing TBSM was highly specific toward LDs. Therefore, this preliminary result suggests that TBSM could be used in locating the LDs in the yolk sac, which is essential for observing LDs related biological processes toward in vivo level.

Example 10—Photophysical Properties of TBSMCN

Figure 23A:
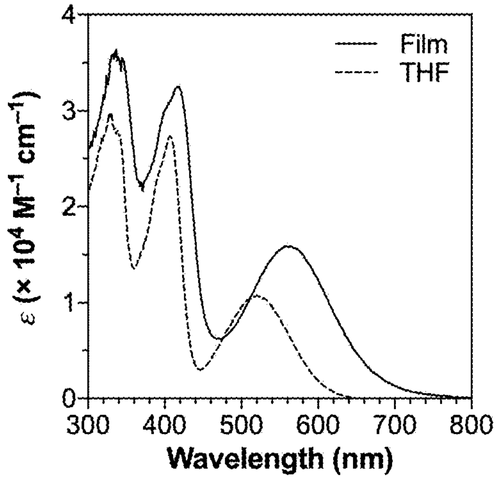
FIG. 23A Absorption spectra of TBSMCN in THF (c=$10^{-5}$ mol/L) and as film.
Figure 23B:
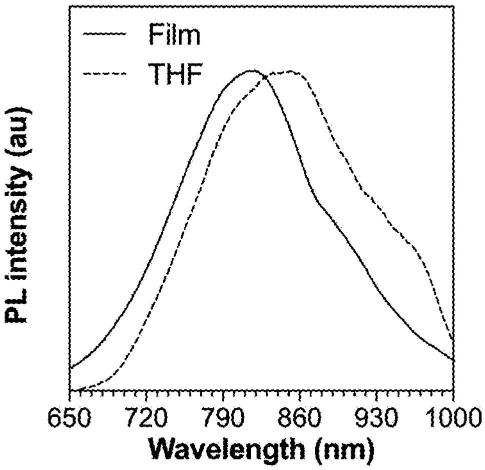
FIG. 23B PL spectra of TBSMCN in THF (c=$10^{-5}$ mol/L) and as film, $\lambda_{ex}$=530 nm.
Figure 24A:
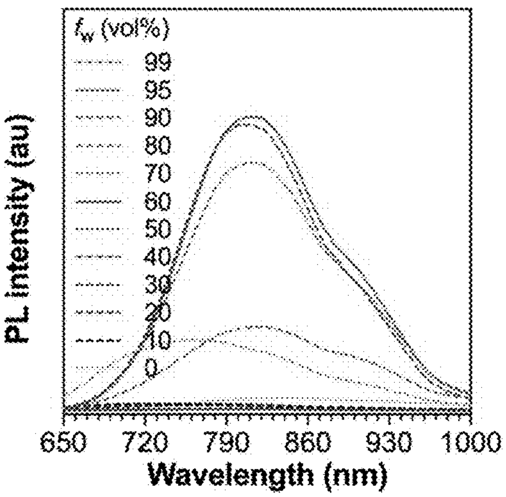
FIG. 24A PL spectra of TBSMCN in $H_2O$/THF mixtures with different water fractions ($f_w$). Concentration: $10^{-5}$ M; $\lambda_{ex}$=530 nm.
Figure 24B:
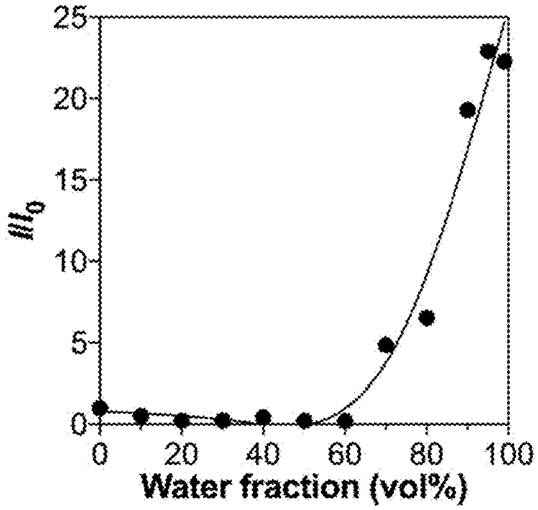
FIG. 24B Plots of relative emission intensity ($I/I_0$) versus the composition of the mixture, where $I_0$=PL intensity in pure THF at $\lambda_{em}$=810 nm.

The photophysical properties of TBSMCN were investigated. In THF solution, it showed three absorption peaks at 320 nm, 400 nm and 520 nm, in which the first one could be assigned to a π-π* absorption, the second one arose from the BSM moiety, and the last one was from the intramolecular charge transfer (ICT) absorption. All the three peaks showed red-shift compared with those of TBSM, that may due to the extra electron-withdrawing group CN and different substituent position. In the film, the ICT peak further red shifted to 580 nm. TBSMCN exhibited NIR emission film state with high QY about 10% (FIG. 23A and FIG. 23B). TBSMCN was also AIE-active, showing increased PL emission intensity in the mixture of THF and water as the water fraction increased (FIG. 24A and FIG. 24B).

Example 11—Single Crystal Structure

Figure 25A:
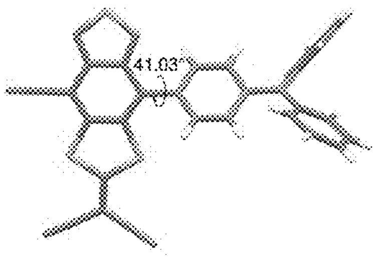
FIG. 25A Single crystal structure of TBSMCN.
Figure 25B:
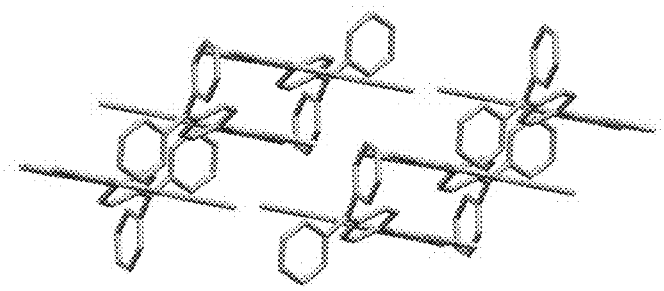
FIG. 25B Packing mode of TBSMCN.
Figure 26A:
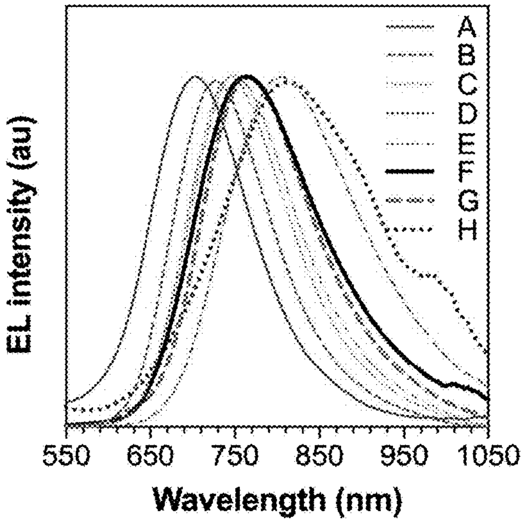
FIG. 26A The EL spectra.
Figure 26B:
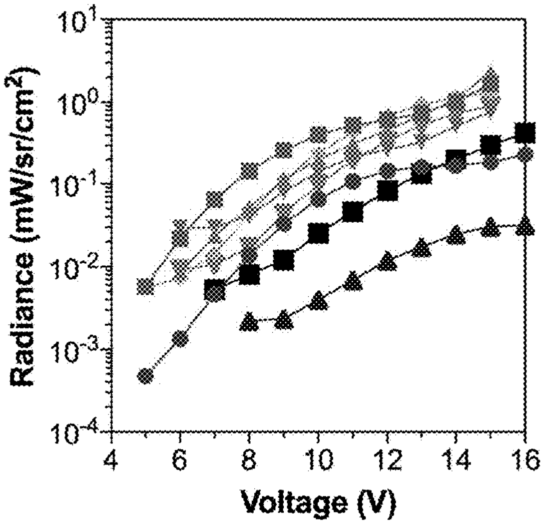
FIG. 26B Radiance versus voltage.
Figure 26C:
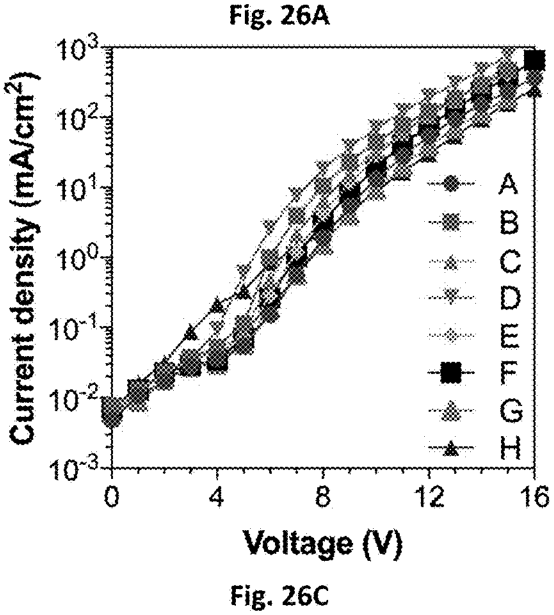
FIG. 26C Current density versus voltage and FIG. 26D EQE versus current density.
Figure 26D:
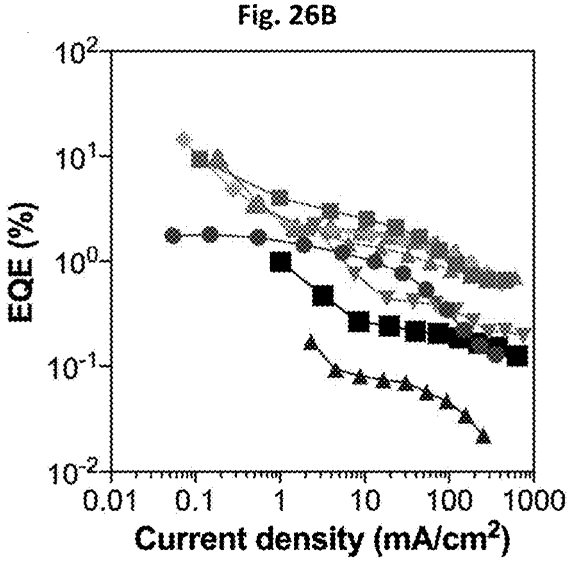

The single crystal of TBSMCN was also achieved for better understanding its properties. It had a twisting angle, about 41.03°, between the TPA and acceptor core. In the packing mode, the planar cores were separated by the TPA part to avoid long range π-π stacking, which is the main reason for fluorescence quenching. Therefore, TBSMCN showed high QY even in the solid state (FIG. 25A and FIG. 25B).

Example 12—OLED Device Performance

Considering the excellent property of TBSMCN, it was applied to fabricaAted solution-processed OLED devices. The structures were indium tin oxide (ITO)/m-PEDOT:PSS (70 nm)/emitting layer (EML)/DPEPO (10 nm)/TmPyPB (50 nm)/Liq (1 nm)/Al (100 nm). In different device structure, the EML is (A) mCP:TBSMCN (95:5, 40 nm); (B) mCP:TBSMCN (75:25, 40 nm); (C) mCP:TBSMCN (50:50, 40 nm); (D) mCP:TBSMCN (0:100, 40 nm); (E) mCP:PCAQC0.5:TBSMCN (30:20:50, 40 nm); (F) mCP:Ir(MDQ)2acac:TBSMCN (30:20:50, 40 nm); (G) mCP:Nato-QD-R:TBSMCN (30:20:50, 40 nm); (H) PABPC5 (10 nm)/TBSMCN (40 nm). Some of the devices showed excellent results. For doped devices, highest EQE of 14.25% was achieved, which peaked at 750 nm. And for non-doped devices, highest EQE of 2.17% was realized, which peaked at 804 nm. The results showing the new molecules has a very promising application in OLED devices (FIG. 26A, FIG. 26B, FIG. 26C and FIG. 26D).

Example 13—Photophysical Properties of TBSMPy and TBSMDPy

The photophysical properties of TBSMPy and TBSMDPy were studied. In the film state, they had absorption peaks around 400 nm and 580 nm. The emission peaks were at 750 nm with high QY of 16.3% and 25.0% for TBSMPy and TBSMDPy, respectively (FIGS. 27 and 28).

The above embodiments are only used to illustrate the principles of the present invention, and they should not be construed as to limit the present invention in any way. The above embodiments can be modified by those with ordinary skill in the art without departing from the scope of the present invention as defined in the following appended claims.

What is claimed is:

1. A fluorescent compound exhibiting aggregation induced emission properties, the fluorescent compound having formula (I) or formula (II):

(I)

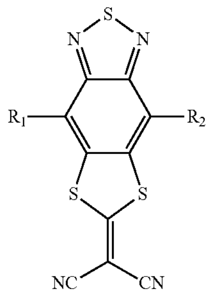

(II)

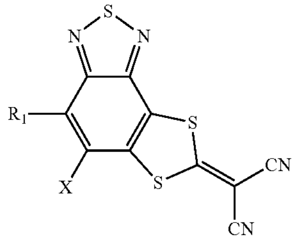

wherein $R_1$ is selected from the group consisting of:

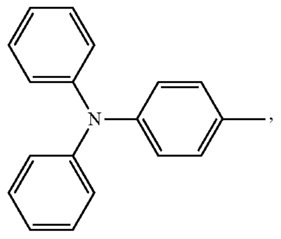

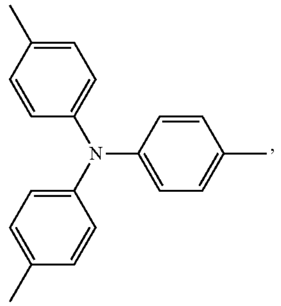

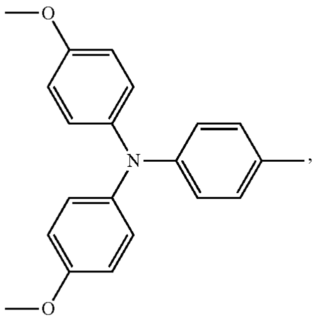

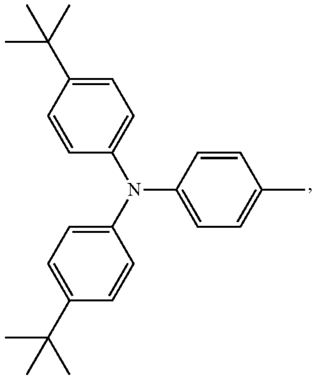

-continued

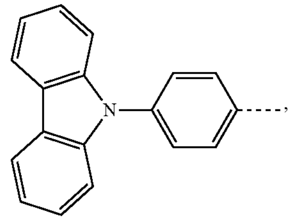

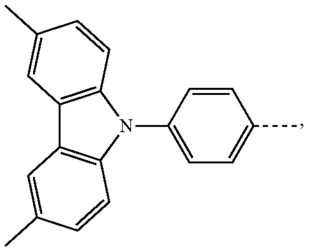

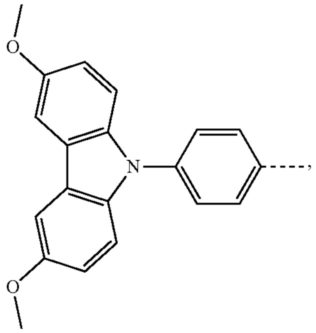

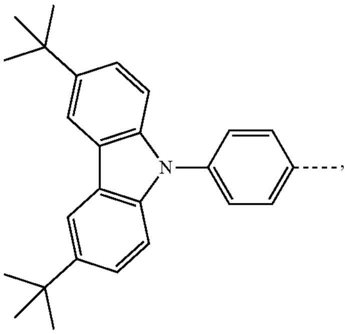

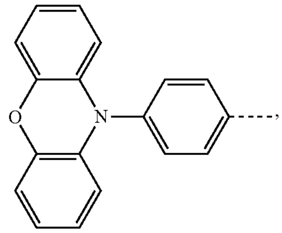

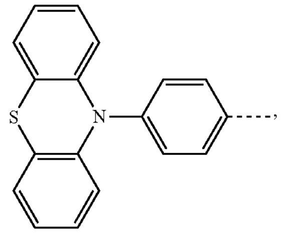

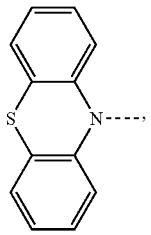

and

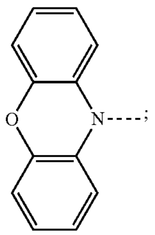

wherein $R_2$ is selected from the group consisting of:

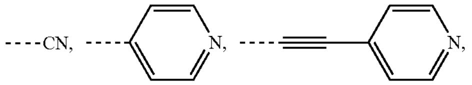

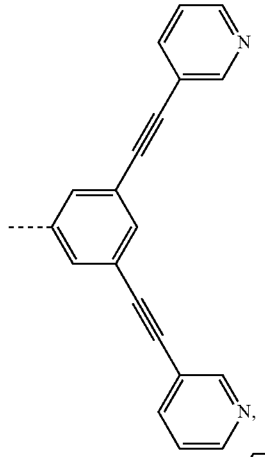

and

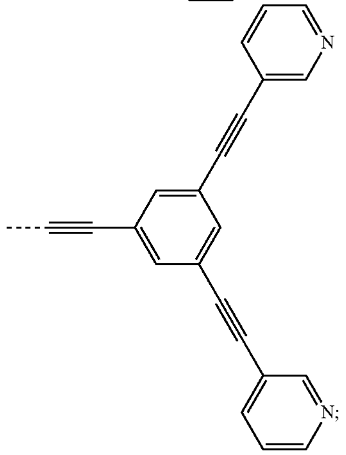

wherein X is selected from the group consisting of —H, —F, and —Cl; and wherein $R_1$ is a tertiary aromatic amine group for introducing high steric twisting between $R_1$ and the benzothiazole core structure, while $R_2$ is nitrile based or pyridine based linear group for introducing low steric twisting between $R_2$ and the benzothiazole core structure, which contributes to a locked nonplanar conformation of the fluorescent compound in the aggregate state, by avoiding the strong intermolecular π-π interactions, and to make the fluorescent compound exhibit aggregation-induced emission (AIE) properties.

2. The fluorescent compound of claim 1, wherein the fluorescent compound comprises one or more compounds selected from the group consisting of:

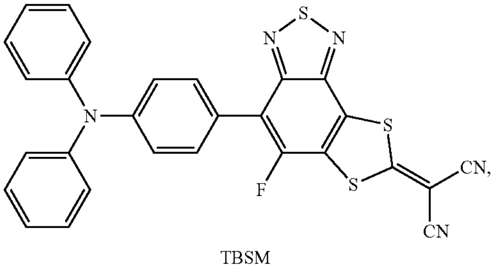

TBSM

-continued

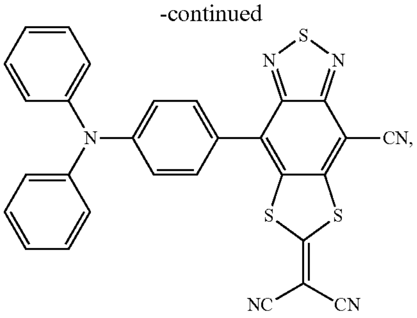

TBSMCN

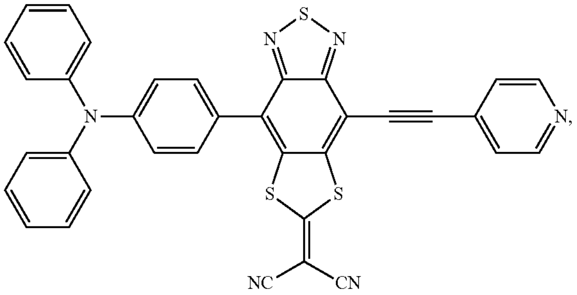

TBSMPy and

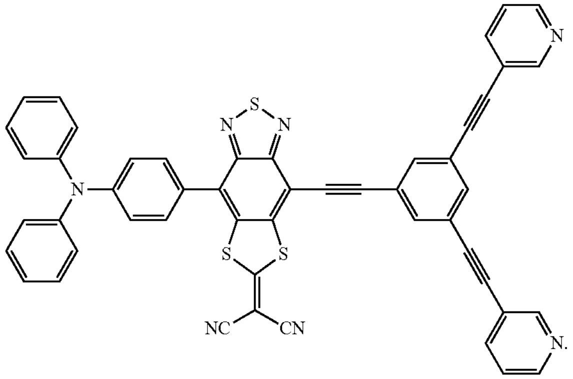

TBSMDPy

3. The fluorescent compound of claim 1, wherein the fluorescent compound shows bright emission in the aggregate state by the avoidance of strong intermolecular π-π interactions via the locked nonplanar conformation.

4. The fluorescent compound of claim 1, wherein the fluorescent compound shows an intramolecular charge transfer (ICT) effect in solution and an aggregation-induced emission (AIE) property in the aggregate state.

5. A method of cellular imaging, comprising:

contacting a target cell with the fluorescent compound of claim 1; and identifying a target of interest in the target cell using an imaging method.

6. The method of claim 5, wherein the target of interest comprises lipid droplets.

7. The method of claim 5, wherein the imaging method is selected from the group consisting of fluorescence microscopy and confocal laser scanning microscopy.

8. The method of claim 7, wherein the fluorescence microscopy comprises two-photon fluorescence imaging.

9. The method of claim 5, wherein the target cell is a live cell.

10. The method of claim 9, wherein the target cell is in live tissue.

11. The method of claim 9, wherein the target cell is in live embryos.

12. An organic electroluminescent device comprising a light-emitting layer comprising:

at least one host material; and at least one thermally activated delayed fluorescence (TADF) material comprising the fluorescent compound of claim 1.

13. The organic electroluminescent device of claim 12, wherein the organic electroluminescent device is selected from the group consisting of an organic light emitting diode, a light emitting electrochemical cell, and a light-emitting transistor.

* * * * *